(12) United States Patent
Hansen et al.

(10) Patent No.: US 11,505,767 B2
(45) Date of Patent: Nov. 22, 2022

(54) METHODS FOR CLEANSING MEDICAL DEVICES

(71) Applicant: Novozymes A/S, Bagsvaerd (DK)

(72) Inventors: Rasmus Rune Hansen, Ballerup (DK); Rune Nygaard Monrad, Hillerod (DK); Rebecca Munk Vejborg, Holte (DK); Dorotea Raventos Segura, Rungsted (DK)

(73) Assignee: Novozymes A/S, Bagsvaerd (DK)

( * ) Notice: Subject to any disclaimer, the term of this patent is extended or adjusted under 35 U.S.C. 154(b) by 294 days.

(21) Appl. No.: 16/759,648

(22) PCT Filed: Oct. 31, 2018

(86) PCT No.: PCT/EP2018/079855
§ 371 (c)(1),
(2) Date: Apr. 27, 2020

(87) PCT Pub. No.: WO2019/086532
PCT Pub. Date: May 9, 2019

(65) Prior Publication Data
US 2020/0291331 A1 Sep. 17, 2020

(30) Foreign Application Priority Data
Nov. 1, 2017 (EP) .................... 17199591

(51) Int. Cl.
*B08B 3/08* (2006.01)
*C11D 3/386* (2006.01)
*C11D 1/65* (2006.01)
*C11D 3/00* (2006.01)
*C11D 3/30* (2006.01)
*C11D 3/48* (2006.01)
*C11D 11/00* (2006.01)
*C12N 9/24* (2006.01)
*C11D 1/14* (2006.01)
*C11D 1/62* (2006.01)

(52) U.S. Cl.
CPC ............ *C11D 3/38636* (2013.01); *C11D 1/65* (2013.01); *C11D 3/0005* (2013.01); *C11D 3/30* (2013.01); *C11D 3/48* (2013.01); *C11D 11/0023* (2013.01); *C12N 9/2402* (2013.01); *C12Y 302/01052* (2013.01); *A61L 2202/24* (2013.01); *C11D 1/143* (2013.01); *C11D 1/146* (2013.01); *C11D 1/62* (2013.01); *C11D 3/386* (2013.01)

(58) Field of Classification Search
CPC ........................................ B08B 3/08
USPC ........................................ 510/392
See application file for complete search history.

(56) References Cited

FOREIGN PATENT DOCUMENTS

| EP | 0425017 A2 | 5/1991 | |
| WO | 2004/061117 A2 | 7/2004 | |
| WO | WO-2004061117 A2 * | 7/2004 | ............ C07H 21/04 |
| WO | 2008/157350 A2 | 12/2008 | |
| WO | 2009/121183 A1 | 10/2009 | |

* cited by examiner

*Primary Examiner* — Gregory E Webb
(74) *Attorney, Agent, or Firm* — Elias Lambiris

(57) ABSTRACT

The present invention relates to compositions such as cleaning compositions comprising a mix of enzymes. The invention further relates, use of compositions comprising such enzymes in cleaning processes.

19 Claims, No Drawings
Specification includes a Sequence Listing.

METHODS FOR CLEANSING MEDICAL DEVICES

CROSS-REFERENCE TO RELATED APPLICATIONS

This application is a 35 U.S.C. 371 national application of international application no. PCT/EP2018/079855 filed Oct. 31, 2018 which claims priority or the benefit under 35 U.S.C. 119 of European application no.17199591.3 filed Nov. 1, 2017 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

The present invention relates to compositions such as cleaning compositions comprising a mix of enzymes. The invention further relates, use of compositions comprising such enzymes in cleaning processes and/or for cleaning of organic soiling, methods for removal or reduction of organic soiling.

DESCRIPTION OF THE RELATED ART

Surfaces of medical and surgical equipment may become soiled with many different types of organic soiling e.g. from body tissue or feces. Such soils may include proteins from blood and muscular tissue, fats e.g. from adipose tissue and carbohydrates e.g. from feces. Other types of organic soiling may be dead tissue cells, or biofilm, EPS (extracellular polysaccharide substance), produced by various microorganisms. Organic stains may compose of different molecules such as polysaccharides, macromolecules, and proteins. Biofilm is produced by populations of bacteria or fungi growing attached to a surface. Bacteria growing in biofilms exhibit increased resistance to antimicrobial agents and are difficult to remove. Many biofilms are embellished in a slimy layer termed EPS. Biofilm EPS is a polymeric conglomeration generally composed of proteins, macromolecules and polysaccharides. The presence of biofilm on medical devices in particular medical indwelling devises and intravascular catheters is of particular concern in the clinic. Kaplan et. al. (WO04061117 A2) has shown that compositions comprising beta-N-acetylglucosaminidase enzymes promotes detachment of bacterial or fungal cells from biofilm. The medical industry utilizes devices that are required to be cleaned to remove soil, including organic soil such as blood, faces, dead cells and biofilm from the device. The presence of organic material or soil may contribute to the failure of disinfection by harboring embedded microbes and preventing the penetration of the germicide. Thus, there is a need for efficient cleaning compositions and method for cleaning of medical devices. Although enzymes have been used to reduce or remove biofilms in industrial and clinic environments, enzymes suitable for cleaning of e.g. medical devices need to be compatible with compositions used for cleaning of such devices. Thus, enzymes suitable for cleaning of e.g. medical devices are preferably those which remove or reduce organic stains such as biofilm and components hereof and are stable in presence of detergent components such as surfactants. The present invention provides cleaning compositions comprising hexosaminidases having, beta-N-acetylglucosaminidase activity for use for detachment of bacterial cells in biofilm on surfaces, such as medical devices. The present invention also relates to methods for detachment, removal or reduction of biofilm cells of bacteria or fungi using a cleaning composition comprising a hexosaminidase of the invention.

SUMMARY OF THE INVENTION

The present invention relates to a method of cleaning a medical device, wherein the method comprises
 a) contacting the medical device with the composition comprising a hexosaminidase having beta-N-acetylglucosaminidase activity, for a period effective to clean the medical device;
 b) cleaning, the medical device; and
 c) optionally disinfect the medical device.

The invention further relates to the use of a composition comprising a hexosaminidase having beta-N-acetylglucosaminidase activity and at least one adjunct ingredient for cleaning of a medical device.

The invention further relates to a method for inhibiting, preventing or treating bacterial or fungal infections comprising, administering to an organism a composition comprising at least one hexosaminidase having beta-N-acetylglucosaminidase activity selected from the group consisting of;
 i) a polypeptide comprising the amino acid sequence shown in SEQ ID NO: 1 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 ii) a polypeptide comprising the amino acid sequence shown in SEQ ID NO: 2 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 iii) a polypeptide comprising the amino acid sequence shown in SEQ ID NO: 3 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 iv) a polypeptide comprising the amino acid sequence shown in SEQ ID NO: 4 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 v) a polypeptide comprising the amino acid sequence shown in SEQ ID NO: 5 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 vi) a polypeptide comprising the amino acid sequence shown in SEQ ID NO: 6 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 vii) a polypeptide comprising the amino acid sequence shown in SEQ ID NO: 7 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, viii) a polypeptide comprising the amino acid sequence shown in SEQ ID NO: 8 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, ix) a polypeptide comprising the amino acid sequence shown in SEQ ID NO: 9 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, x) a polypeptide comprising the amino acid sequence shown in SEQ ID NO: 10 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xi) a polypeptide comprising the amino acid sequence shown in SEQ ID NO: 11 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xii) a polypeptide comprising the amino acid sequence shown in SEQ ID NO: 12 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xiii) a polypeptide comprising the amino acid sequence shown in SEQ ID NO: 13 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xiv) a polypeptide comprising the amino acid sequence shown in SEQ ID NO: 14 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xv) a polypeptide comprising the amino acid sequence shown in SEQ ID NO: 15 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xvi) a polypeptide comprising the amino acid sequence shown in SEQ ID NO: 16 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xvii) a polypeptide comprising the amino acid sequence shown in SEQ ID NO: 17 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xviii) a polypeptide comprising the amino acid sequence shown in SEQ ID NO: 18 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xix) a polypeptide comprising the amino acid sequence shown in SEQ ID NO: 19 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xx) a polypeptide comprising the amino acid sequence shown in SEQ ID NO: 20 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxi) a polypeptide comprising the amino acid sequence shown in SEQ ID NO: 21 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxii) a polypeptide comprising the amino acid sequence shown in SEQ ID NO: 22 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxiii) a polypeptide comprising the amino acid sequence shown in SEQ ID NO: 23 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxiv) a polypeptide comprising the amino acid sequence shown in SEQ ID NO: 24 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, such that detachment of bacterial or fungal cells from a biofilm is promoted.

The invention further relates to the use of a composition comprising a hexosaminidase having beta-N-acetylglucosaminidase activity and at least one adjunct ingredient for cleaning of a medical device, wherein the hexosaminidase having beta-N-acetylglucosaminidase activity is selected from the group of polypeptides having at least 60%, at least 65%, at least 70%, at least 75%, at least 80%, at least 85%, at least 90%, at least 95%, at least 96%, at least 97%, at least 98%, at least 99% or at least 100% sequence identity to the amino acid sequence shown in SEQ ID NOs: 1, 2, 3, 4, 5, 6, 7, 8, 9, 10, 11, 12, 13, 14, 15, 16, 17, 18, 19, 20, 21, 22, 23 and 24

The invention further relates to a kit comprising a hexosaminidase an adjunct ingredient and instructions for use.

DETAILED DESCRIPTION OF THE INVENTION

Various enzymes are applied in cleaning processes each targeting specific types of soiling such as protein, starch and grease soiling. Enzymes are standard ingredients in detergents for laundry and dish wash. The effectiveness of these commercial enzymes provides detergents which removes much of the soiling. However, organic matters such as EPS (extracellular polymeric substance) comprised in much biofilm constitute a challenging type of soiling due to the complex nature of such organic matters. EPS is mostly composed of polysaccharides (exopolysaccharides) and proteins, but include other macro-molecules such as eDNA, lipids and other organic substances. A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls. Biofilms are attributed to the pathogenesis of many infections in humans and are a significant problem in industry in terms of biofouling of exposed surfaces where biofilm colonisation can form the base component of a localised ecosystem which can disrupt and interfere with industrial processes and components. The enzymes of the invention are capable of reduce and/or remove components of the biofilm such as polysaccharides e.g. PNAG (Poly-N-acetyl glucosamine) in e.g. EPS layer and thus reduce or remove e.g. biofilm e.g. by detachment of bacterial cells in biofilm on surfaces, such as medical devices. Hexosaminidases, such as dispersins are known for degrading PNAG a major component of most biofilm EPS. Compositions comprising hexosaminidases has shown effective promote detachment of bacterial cells from a biofilm on various surfaces (WO04061117 A2). To be effective in a cleaning process the enzymes need to be compatible with the cleaning/detergent components presence in the cleaning composition. Thus, a suitable enzyme for e.g. cleaning of medical devices have the capability of reducing or removing organic matter such as PNAG in e.g. biofilm and be stable in a composition suitable for cleaning. Enzyme such as hexosaminidases suitable for medical cleaning should be effective in reducing or removal of the relevant stain and be stable in compositions suitable for medical cleaning. Such compositions usually comprise surfactants, in particular anionic surfactants frequently used anionic surfactants includes linear alkylbenzenesulfonates (LAS), alpha-olefin-sulfonates (AOS) and alcohol ethersulfates (AES or AEOS or FES, also known as alcohol ethoxysulfates or fatty alcohol ether sulfates). The hexosaminidase used according to the present invention have improved stability in the presence of e.g. LAS compared to the hexosaminidases previously used for cleaning medical devices. The hexosaminidases having beta-N-acetylglucosaminidase activity are particular useful in cleaning of medical devices as they combine the ability to reduce or remove organic stains e.g. comprising PNAG with stability in compositions comprising anionic surfactants.

The polypeptides suitable for use in medical cleaning and in compositions for medical cleaning are described below. The polypeptides for use in methods and compositions according to the invention are hexosaminidases, preferably dispersins. The term "hexosaminidases" means a polypeptide having hexosaminidase activity (hexosaminidases), and includes EC 3.2.1. e.g. that catalyzes the hydrolysis of N-acetyl-D-hexosamine or N-acetyl-glucosamine polymers found e.g. in biofilm. The term includes dispersins and includes polypeptides having N-acetylglucosaminidase activity and β-N-acetylglucosamininidase activity. The term "polypeptide having hexosaminidase activity" may be used interchangeably with the term hexosaminidases and similar the term "polypeptide having β-N-acetylglucosaminidase activity" may be used interchangeably with the term β-N-acetylglucosamininidases. For the purposes of the present invention, hexosaminidase activity is determined according to the procedure described in Assay 1 or 2. Hexosaminidases having β-N-acetylglucosamininidase activity includes dispersins. The term "dispersin" and the abbreviation "Dsp" means a polypeptide having hexosaminidase activity, EC 3.2.1.—that catalyzes the hydrolysis of β-1,6-glycosidic linkages of N-acetyl-glucosamine polymers (poly-N-acetyl-glucosamine) found e.g. in biofilm. In preferred embodiments of the invention the hexosaminidases are dispersins.

In one aspect, the polypeptide having hexosaminidase activity is a *Terribacillus* polypeptide, e.g., a polypeptide obtained from *Terribacillus saccharophilus*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1 and is obtained from *Terribacillus* preferably *Terribacillus saccharophilus*.

In another aspect, the polypeptide is a *Terribacillus* polypeptide, e.g., a polypeptide obtained from *Terribacillus goriensis*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2 and is obtained from *Terribacillus* preferably *Terribacillus goriensis*.

In another aspect, the polypeptide is a *Terribacillus* polypeptide, e.g., a polypeptide obtained from *Terribacillus saccharophilus*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 3 and is obtained from *Terribacillus* preferably *Terribacillus saccharophilus*.

In another aspect, the polypeptide having hexosaminidase activity is a *Terribacillus* polypeptide, e.g., a polypeptide obtained from *Terribacillus saccharophilus*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4 and is obtained from *Terribacillus* preferably *Terribacillus saccharophilus*.

In another aspect, the polypeptide having hexosaminidase activity is a *Terribacillus* polypeptide, e.g., a polypeptide obtained from *Terribacillus saccharophilus*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 5 and is obtained from *Terribacillus* preferably *Terribacillus saccharophilus*.

In another aspect, the polypeptide is a *Curtobacterium* polypeptide, e.g., a polypeptide obtained from *Curtobacterium oceanosedimentum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 6 and is obtained from *Curtobacterium* preferably *Curtobacterium oceanosedimentum*.

In another aspect, the polypeptide is a *Curtobacterium* polypeptide, e.g., a polypeptide obtained from *Curtobacterium flaccumfaciens*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 7 and is obtained from *Curtobacterium* preferably *Curtobacterium flaccumfaciens*.

In another aspect, the polypeptide is a *Curtobacterium* polypeptide, e.g., a polypeptide obtained from *Curtobacterium luteum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 8 and is obtained from *Curtobacterium* preferably *Curtobacterium luteum*.

In another aspect, the polypeptide is a *Curtobacterium* polypeptide, e.g., a polypeptide obtained from *Curtobacterium oceanosedimentum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 9 and is obtained from *Curtobacterium* preferably *Curtobacterium oceanosedimenturn*.

In another aspect, the polypeptide is a *Curtobacterium* polypeptide, e.g., a polypeptide obtained from *Curtobacterium* Leaf154. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 10 and is obtained from *Curtobacterium* preferably *Curtobacterium* Leaf154.

In another aspect, the polypeptide is a *Aggregatibacter* polypeptide, e.g., a polypeptide obtained from *Aggregatibacter actinomycetemcomitans*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 11 and is obtained from *Aggregatibacter* preferably *Aggregatibacter actinomycetemcomitans*.

In another aspect, the polypeptide is a *Haemophilus* polypeptide, e.g., a polypeptide obtained from *Haemophilus sputorum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 12 and is obtained from *Haemophilus* preferably *Haemophilus sputorum*.

In another aspect, the polypeptide is a *Actinobacillus* polypeptide, e.g., a polypeptide obtained from *Actinobacillus suis*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 13 and is obtained from *Actinobacillus* preferably *Actinobacillus suis*.

In another aspect, the polypeptide is a *Actinobacillus* polypeptide, e.g., a polypeptide obtained from *Actinobacillus capsulatus* DSM 19761. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 14 and is obtained from *Actinobacillus* preferably *Actinobacillus capsulatus* DSM 19761.

In another aspect, the polypeptide is a *Actinobacillus* polypeptide, e.g., a polypeptide obtained from *Actinobacillus equuli* subsp. *equuli*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 15 and is obtained from *Actinobacillus* preferably *Actinobacillus equuli* subsp. *equuli*.

In another aspect, the polypeptide is a *Aggregatibacter* polypeptide, e.g., a polypeptide obtained from *Aggregatibacter actinomycetemcomitans*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 16 and is obtained from *Aggregatibacter* preferably *Aggregatibacter actinomycetemcomitans*.

In another aspect, the polypeptide is a *Aggregatibacter* polypeptide, e.g., a polypeptide obtained from *Aggregatibacter actinomycetemcomitans*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 17 and is obtained from *Aggregatibacter* preferably *Aggregatibacter actinomycetemcomitans*.

In another aspect, the polypeptide is a *Actinobacillus* polypeptide, e.g., a polypeptide obtained from *Actinobacillus pleuropneumoniae*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 18 and is obtained from *Actinobacillus* preferably *Actinobacillus pleuropneumoniae*.

In another aspect, the polypeptide is a *Lactobacillus* polypeptide, e.g., a polypeptide obtained from *Lactobacillus paraplantarum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 19 and is obtained from *Lactobacillus* preferably, *Lactobacillus paraplantarum*.

In another aspect, the polypeptide is a *Lactobacillus* polypeptide, e.g., a polypeptide obtained from *Lactobacillus apinorum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 20 and is obtained from *Lactobacillus* preferably, *Lactobacillus apinorum*.

In another aspect, the polypeptide is a *Lactobacillus* polypeptide, e.g., a polypeptide obtained from *Lactobacillus*

*paraplantarum*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 21 and is obtained from *Lactobacillus* preferably, *Lactobacillus paraplantarum*.

In another aspect, the polypeptide is a *Streptococcus* polypeptide, e.g., a polypeptide obtained from *Streptococcus merionis*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 22 and is obtained from *Streptococcus* preferably, *Streptococcus merionis*.

In another aspect, the polypeptide is a *Staphylococcus* polypeptide, e.g., a polypeptide obtained from *Staphylococcus cohnii*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 23 and is obtained from *Staphylococcus* preferably, *Staphylococcus cohnii*.

In another aspect, the polypeptide is a *Staphylococcus* polypeptide, e.g., a polypeptide obtained from *Staphylococcus fleurettii*. In a preferred aspect, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 24 and is obtained from *Staphylococcus* preferably, *Staphylococcus fleurettii*.

The present invention relates to methods for cleaning medical devices or the use of compositions comprising hexosaminidases having beta-N-acetylglucosaminidase activity for cleaning medical devices.

One embodiment relates to the use of a composition comprising a hexosaminidase having beta-N-acetylglucosaminidase activity and at least one adjunct ingredient for cleaning of a medical device, wherein the hexosaminidase having beta-N-acetylglucosaminidase activity is selected from the group of polypeptides having at least 60%, at least 65%, at least 70%, at least 75%, at least 80%, at least 85%, at least 90%, at least 95%, at least 96%, at least 97%, at least 98%, at least 99% or at least 100% sequence identity to the amino acid sequence shown in SEQ ID NOs: 1, 2, 3, 4, 5, 6, 7, 8, 9, 10, 11, 12, 13, 14, 15, 16, 17, 18, 19, 20, 21, 22, 23 and 24. One aspect of the invention relates to a method of cleaning a medical device, wherein the method comprises
 a) contacting the medical device with the composition comprising a hexosaminidase having beta-N-acetylglucosaminidase activity, for a period effective to clean the medical device;
 b) cleaning, the medical device; and
 c) optionally disinfect the medical device.

One embodiment of the invention relates to a method of cleaning a medical device, wherein the method comprises
 a) contacting the medical device with the composition comprising a hexosaminidase having beta-N-acetylglucosaminidase activity, for a period effective to clean the medical device;
 b) cleaning, the medical device; and optionally disinfect the medical device, wherein the hexosaminidase having beta-N-acetylglucosaminidase activity is selected from the group consisting of;
 i) a polypeptide comprising the amino acid sequence shown in SEQ ID NO: 1 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 ii) a polypeptide comprising the amino acid sequence shown in SEQ ID NO: 2 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 iii) a polypeptide comprising the amino acid sequence shown in SEQ ID NO: 3 or a polypeptide having at least 60%, at least 65%, at least 70%, at least 75%, at least 80%, at least 85%, at least 90%, at least 95%, at least 96%, at least 97%, at least 98%, at least 99% or at least 100% % sequence identity hereto,
 iv) a polypeptide comprising the amino acid sequence shown in SEQ ID NO: 4 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 v) a polypeptide comprising the amino acid sequence shown in SEQ ID NO: 5 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 vi) a polypeptide comprising the amino acid sequence shown in SEQ ID NO: 6 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 vii) a polypeptide comprising the amino acid sequence shown in SEQ ID NO: 7 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 viii) a polypeptide comprising the amino acid sequence shown in SEQ ID NO: 8 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 ix) a polypeptide comprising the amino acid sequence shown in SEQ ID NO: 9 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 x) a polypeptide comprising the amino acid sequence shown in SEQ ID NO: 10 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto,
 xi) a polypeptide comprising the amino acid sequence shown in SEQ ID NO: 11 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xii) a polypeptide comprising the amino acid sequence shown in SEQ ID NO: 12 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xiii) a polypeptide comprising the amino acid sequence shown in SEQ ID NO: 13 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xiv) a polypeptide comprising the amino acid sequence shown in SEQ ID NO: 14 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xv) a polypeptide comprising the amino acid sequence shown in SEQ ID NO: 15 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xvi) a polypeptide comprising the amino acid sequence shown in SEQ ID NO: 16 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xvii) a polypeptide comprising the amino acid sequence shown in SEQ ID NO: 17 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xviii) a polypeptide comprising the amino acid sequence shown in SEQ ID NO: 18 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xix) a polypeptide comprising the amino acid sequence shown in SEQ ID NO: 19 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xx) a polypeptide comprising the amino acid sequence shown in SEQ ID NO: 20 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxi) a polypeptide comprising the amino acid sequence shown in SEQ ID NO: 21 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxii) a polypeptide comprising the amino acid sequence shown in SEQ ID NO: 22 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, xxiii) a polypeptide comprising the amino acid sequence shown in SEQ ID NO: 23 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, and xxiv) a polypeptide comprising the amino acid sequence shown in SEQ ID NO: 24 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, preferably wherein the composition is administered as a coating on a medical device implanted in the organism.

One embodiment of the invention relates to a method of cleaning a medical device, wherein the method comprises
a) contacting the medical device with the composition comprising a hexosaminidase having beta-N-acetylglucosaminidase activity, for a period effective to clean the medical device;
b) cleaning, the medical device; and optionally disinfect the medical device, wherein the hexosaminidase having beta-N-acetylglucosaminidase activity is obtained from *Terribacillus* and is selected from the group consisting of; a polypeptide comprising the amino acid sequence shown in SEQ ID NOs: 1, 2, 3, 4, 5 and a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto.

One embodiment of the invention relates to a method of cleaning a medical device, wherein the method comprises
a) contacting the medical device with the composition comprising a hexosaminidase having beta-N-acetylglucosaminidase activity, for a period effective to clean the medical device;
b) cleaning, the medical device; and optionally disinfect the medical device, wherein the hexosaminidase having beta-N-acetylglucosaminidase activity is obtained from *Curtobacterium* and is selected from the group consisting of; a polypeptide comprising the amino acid sequence shown in SEQ ID NOs: 6, 7, 8, 9, 10 and a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto.

One embodiment of the invention relates to a method of cleaning a medical device, wherein the method comprises
a) contacting the medical device with the composition comprising a hexosaminidase having beta-N-acetylglucosaminidase activity, for a period effective to clean the medical device;
b) cleaning, the medical device; and optionally disinfect the medical device, wherein the hexosaminidase having beta-N-acetylglucosaminidase activity is obtained from *Aggregatibacter* or *Actinobacillus* and belong to the Dispersin B group of dispersins and is selected from the group consisting of; a polypeptide comprising the amino acid sequence shown in SEQ ID NOs: 11, 12, 13, 14, 15, 16, 17, 18 and a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto.

One embodiment of the invention relates to a method of cleaning a medical device, wherein the method comprises
a) contacting the medical device with the composition comprising a hexosaminidase having beta-N-acetylglucosaminidase activity, for a period effective to clean the medical device;
b) cleaning, the medical device; and optionally disinfect the medical device, wherein the hexosaminidase having beta-N-acetylglucosaminidase activity is obtained from *Lactobacillus* and is selected from the group consisting of; a polypeptide comprising the amino acid sequence shown in SEQ ID NOs: 19, 20, 21 and a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto.

One embodiment of the invention relates to a method of cleaning a medical device, wherein the method comprises
a) contacting the medical device with the composition comprising a hexosaminidase having beta-N-acetylglucosaminidase activity, for a period effective to clean the medical device;
b) cleaning, the medical device; and optionally disinfect the medical device, wherein the hexosaminidase having beta-N-acetylglucosaminidase activity is obtained from *Streptococcus* and comprises a polypeptide comprising the amino acid sequence shown in SEQ ID NO: 22 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto.

One embodiment of the invention relates to a method of cleaning a medical device, wherein the method comprises
a) contacting the medical device with the composition comprising a hexosaminidase having beta-N-acetylglucosaminidase activity, for a period effective to clean the medical device;
b) cleaning, the medical device; and optionally disinfect the medical device, wherein the hexosaminidase having beta-N-acetylglucosaminidase activity is obtained from *Staphylococcus* and comprises a polypeptide comprising the amino acid sequence shown in SEQ ID NOs: 23, 24 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto.

One embodiment relates to the use of a hexosaminidase having beta-N-acetylglucosaminidase activity, preferably a dispersin, for cleaning of a medical device. One embodiment relates to the use of a hexosaminidase having beta-N-acetylglucosaminidase activity, preferably a dispersin, for cleaning of a medical device, wherein the medical device is selected from the group consisting of a catheter such as a central venous catheter, intravascular catheter, urinary catheter, Hickman catheter, peritoneal dialysis catheter, endrotracheal catheter, endoscopes, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument A composition of the present invention is suitable for cleaning of a medical device. One aspect of the invention relates to the use of a composition comprising a hexosaminidase having beta-N-acetylglucosaminidase activity, preferably a dispersin and at least one adjunct ingredient for cleaning of a medical device. One aspect of the invention relates to the use of a composition comprising a hexosaminidase and at least one surfactant for cleaning a medical device. The adjunct is preferably selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers. The composition may be an anti-biofouling composition and the composition may be a pharmaceutical or cleaning composition. One embodiment relates to the use of a composition for cleaning a medical device, wherein the composition comprises;
a) at least 0.01 mg/mL hexosaminidases having beta-N-acetylglucosaminidase activity, preferably a dispersin;
b) at least one cleaning component, preferably selected from surfactants, builders, bleach components, polymers and dispersing agents.

The composition preferably comprises at least one anionic surfactant selected from linear alkylbenzenesulfonates (LAS), alpha-olefinsulfonates (AOS) or alcohol ethersulfates (AES or AEOS or FES, alcohol ethoxysulfates or fatty alcohol ether sulfates). The medical device is preferably selected from the group consisting of a catheter such as a central venous catheter, intravascular catheter, urinary catheter, Hickman catheter, peritoneal dialysis catheter, endrotracheal catheter, endoscopes, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument. The use for medical cleaning may be indwelling medical device characterized in that at least a portion of a patient-contactable surface of the device is coated with composition comprising the hexosaminidase of the invention. The device may be a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

Also provided is a method of inhibiting, preventing or treating bacterial or fungal infections comprising administering to an organism a composition comprising at least one hexosaminidase having beta-N-acetylglucosaminidase activity selected from the group consisting of;

a) a polypeptide comprising the amino acid sequence shown in SEQ ID NO: 1 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, b) a polypeptide comprising the amino acid sequence shown in SEQ ID NO: 2 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, c) a polypeptide comprising the amino acid sequence shown in SEQ ID NO: 3 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, d) a polypeptide comprising the amino acid sequence shown in SEQ ID NO: 4 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, e) a polypeptide comprising the amino acid sequence shown in SEQ ID NO: 5 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, f) a polypeptide comprising the amino acid sequence shown in SEQ ID NO: 6 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, g) a polypeptide comprising the amino acid sequence shown in SEQ ID NO: 7 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, h) a polypeptide comprising the amino acid sequence shown in SEQ ID NO: 8 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, i) a polypeptide comprising the amino acid sequence shown in SEQ ID NO: 9 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, j) a polypeptide comprising the amino acid sequence shown in SEQ ID NO: 10 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, k) a polypeptide comprising the amino acid sequence shown in SEQ ID NO: 11 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, l) a polypeptide comprising the amino acid sequence shown in SEQ ID NO: 12 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, m) a polypeptide comprising the amino acid sequence shown in SEQ ID NO: 13 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, n) a polypeptide comprising the amino acid sequence shown in SEQ ID NO: 14 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, o) a polypeptide comprising the amino acid sequence shown in SEQ ID NO: 15 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, p) a polypeptide comprising the amino acid sequence shown in SEQ ID NO: 16 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, q) a polypeptide comprising the amino acid sequence shown in SEQ ID NO: 17 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, r) a polypeptide comprising the amino acid sequence shown in SEQ ID NO: 18 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, s) a polypeptide comprising the amino acid sequence shown in SEQ ID NO: 19 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, t) a polypeptide comprising the amino acid sequence shown in SEQ ID NO: 20 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, u) a polypeptide comprising the amino acid sequence shown in SEQ ID NO: 21 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, v) a polypeptide comprising the amino acid sequence shown in SEQ ID NO: 22 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, x) a polypeptide comprising the amino acid sequence shown in SEQ ID NO: 23 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, and y) a polypeptide comprising the amino acid sequence shown in SEQ ID NO: 24 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, such that detachment of bacterial or fungal cells from a biofilm is promoted.

The bacterial or fungal infection to be treated is preferably from a bacterium or fungus that produces a biofilm comprising Poly-N-acetylglucosamine (PNAG). The composition comprising a hexosaminidase having beta-N-acetylglucosaminidase activity, preferably dispersin and an adjunct ingredient is preferably administered as a coating on a medical device implanted in the organism.

One embodiment relates to a method of inhibiting, preventing or treating bacterial or fungal infections comprising applying a wound dressing to a subject which is impregnated with a composition comprising a hexosaminidase having beta-N-acetylglucosaminidase activity selected from the group consisting of:

a) a polypeptide comprising the amino acid sequence shown in SEQ ID NO: 1 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, b) a polypeptide comprising the amino acid sequence shown in SEQ ID NO: 2 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, c) a polypeptide comprising the amino acid sequence shown in SEQ ID NO: 3 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, d) a polypeptide comprising the amino acid sequence shown in SEQ ID NO: 4 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, e) a polypeptide comprising the amino acid sequence shown in SEQ ID NO: 5 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, f) a polypeptide comprising the amino acid sequence shown in SEQ ID NO: 6 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, g) a polypeptide comprising the amino acid sequence shown in SEQ ID NO: 7 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, h) a polypeptide comprising the amino acid sequence shown in SEQ ID NO: 8 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, i) a polypeptide comprising the amino acid sequence shown in SEQ ID NO: 9 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, j) a polypeptide comprising the amino acid sequence shown in SEQ ID NO: 10 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, k) a polypeptide comprising the amino acid sequence shown in SEQ ID NO: 11 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, l) a polypeptide comprising the amino acid sequence shown in SEQ ID NO: 12 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, m) a polypeptide comprising the amino acid sequence shown in SEQ ID NO: 13 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, n) a polypeptide comprising the amino acid sequence shown in SEQ ID NO: 14 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, o) a polypeptide comprising the amino acid sequence shown in SEQ ID NO: 15 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, p) a polypeptide comprising the amino acid sequence shown in SEQ ID NO: 16 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, q) a polypeptide comprising the amino acid sequence shown in SEQ ID NO: 17 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, r) a polypeptide comprising the amino acid sequence shown in SEQ ID NO: 18 or a polypeptide having at least 60%, at least 65%, at least 70%, at least 75%, at least 80%, at least 85%, at least 90%, at least 95%, at least 96%, at least 97%, s) a polypeptide comprising the amino acid sequence shown in SEQ ID NO: 19 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, t) a polypeptide comprising the amino acid sequence shown in SEQ ID NO: 20 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, u) a polypeptide comprising the amino acid sequence shown in SEQ ID NO: 21 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, v) a polypeptide comprising the amino acid sequence shown in SEQ ID NO: 22 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, x) a polypeptide comprising the amino acid sequence shown in SEQ ID NO: 23 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, and y) a polypeptide comprising the amino acid sequence shown in SEQ ID NO: 24 or a polypeptide having at least 60%, at least 65%, at least 70%, at least 75%, at least 80%, at least 85%, at least 90%, at least 95%, at least 96%, at least 97%, at least 98%, at least 99% or at least 100% sequence identity hereto, wherein the composition preferably is a pharmaceutical composition.

The choice of additional components is within the skill of the artisan and includes conventional ingredients for the type of composition e.g. cleaning or pharmaceutical compositions, including the exemplary non-limiting components set forth below.

A composition of the invention comprises a polypeptide having β-N-acetylglucosamininidase activity and preferably an adjunct ingredient. The composition may be an anti-biofouling composition and the composition may be a cleaning or pharmaceutical composition. The adjunct ingredient may be any excipient suitable for e.g. cleaning or pharmaceutical compositions. The adjuncts/excipients are within the choice of the skilled artisan. The adjunct ingredient may be selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers. The compositions may be used for detaching biofilm or preventing biofilm formation on surfaces such as medical devices. The medical device may be characterized in that at least a portion of a patient-contactable surface of the device is coated with composition comprising the hexosaminidase of the invention. The medical device may be selected from the group consisting of a catheter such as a central venous catheter, intravascular catheter, urinary catheter, Hickman catheter, peritoneal dialysis catheter, endrotracheal catheter, endoscope or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.

The invention relates to compositions e.g. pharmaceutical or cleaning compositions comprising a hexosaminidase having β-N-acetylglucosamininidase activity and an adjunct ingredient, which may e.g. be one or more cleaning adjuncts e.g. cleaning components or pharmaceutical adjuncts e.g. a pharmaceutical expient. The composition may be used for releasing or detachment of bacterial or fungal cells from a biofilm, reducing, removing a biofilm or preventing biofilm formation.

One aspect relates to a pharmaceutical composition comprising a hexosaminidase having β-N-acetylglucosamininidase activity and a pharmaceutical adjunct ingredient.

A composition of the invention may be an anti-biofouling composition comprising one or more antiparasitic, antiviral, antibacterial or antifungal compound.

The antiparasitic compound can be one or more of a benzazole, such as albendazole, mebendazole and tiabendazole; an azole, such as metronidazole and tinidazole; a macrocycle, such as amphotericin B, rifampin and ivermectin; pyrantel pamoate; diethylcarbamazine; niclosamide; praziquantel; melarsopro; and eflornithine.

The antiviral compound can be one or more of a nucleoside analog reverse transcriptase inhibitor, such as acyclovir, didanosine, stavudine, zidovudine, lamivudine, abacavir, emtricitabine and entecavir; an uncoating inhibitor such as amantadine, rimantadine and pleconaril; a protease inhibitor such as saquinavir, ritonavir, indinavir, nelfinavir and amprenavir; zanamivir; oseltamivir; and rifampin.

The antibacterial compound can be one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

The antifungal compound can be one or more of an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

The anti-biofouling composition preferably comprises a fungicide or biocide preferably a biocidal quaternary ammonium biocide.

The invention relates to an indwelling medical device wherein at least a portion of a patient-contactable surface of the device is coated with a composition hexosaminidase having β-N-acetylglucosamininidase activity.

In one embodiment, the composition is a pharmaceutical composition and in one embodiment the invention relates to an indwelling medical device wherein at least a portion of a patient-contactable surface of the device is coated with a composition hexosaminidase having β-N-acetylglucosamininidase activity. The pharmaceutical composition may be formulated as a liquid, lotion, cream, spray, gel or ointment. The pharmaceutical composition may be for administration to an organism such as an animal patient. The animal patient may be a mammalian patient. The mammalian patient may be a human.

In one embodiment, the composition is a cleaning composition and the adjunct ingredient is selected from at least one or more cleaning component optionally selected from surfactants, builders, bleach components, polymers, dispersing agents.

A composition for cleaning a medical advice preferably comprises at least one surfactant. One aspect of the invention relates to a composition comprising;
a) at least 0.01 mg/mL hexosaminidases having beta-N-acetylglucosaminidase activity;
b) at least one cleaning component, preferably selected from surfactants, builders, bleach components, polymers and dispersing agents.

Surfactants are typical ingredients of cleaning compositions. Surfactants are added to assist removal of soil and are used extensively in the cleaning industry. The anionic surfactants are the most widely used type of surfactants for laundering, dishwashing compositions. Anionic surfactants are particularly good at keeping the dirt, once dislodged, away from fabrics. Thus, a cleaning composition of the invention preferably comprises at least one anionic surfactant, such as alkylbenzene sulfonates, alkyl sulfates or alkyl ether sulfates.

One embodiment of the invention relates to the composition comprising at least one anionic surfactant selected from linear alkylbenzenesulfonates (LAS), alpha-olefinsulfonates (AOS) or alcohol ethersulfates (AES or AEOS or FES, alcohol ethoxysulfates or fatty alcohol ether sulfates).

Not all enzymes are stable in the presence of anionic surfactants. The hexosaminidases obtained from *Terribacillus* e.g. hexosaminidases comprising the amino acid sequence shown in SEQ ID NOs: 1, 2, 3, 4, 5 or closely related homologues or hexosaminidases obtained from *Curtobacterium* e.g. hexosaminidases comprising the amino acid sequence shown in SEQ ID NO: 6, 7, 8, 9, 10 as well as the hexosaminidases from e.g. *Lactobacillus, Streptococcus* or *Staphylococcus* comprising the amino acids sequence shown in SEQ ID NOs: 19, 20, 21, 22, 23, 24 or closely related homologues having beta-N-acetylglucosaminidase activity are stable in the presence of anionic surfactants and are particularly useful in cleaning compositions such as cleaning compositions for cleaning of medical devices. The hexosaminidases of the invention are also stable in the presence of nonionic surfactants nonionic surfactants are less sensitive to water hardness than anionic surfactants, and they foam less strongly and are thus preferred for low foaming compositions. In a preferred aspect of the invention the cleaning composition comprises at least one anionic surfactant in particular linear alkylbenzenesulfonates (LAS), alpha-olefinsulfonates (AOS) or alcohol ethersulfates (AES or AEOS or FES, also known as alcohol ethoxysulfates or fatty alcohol ether sulfates).

One aspect of the invention relates to a composition comprising;
a) at least 0.01 mg/mL hexosaminidases having beta-N-acetylglucosaminidase activity;
b) at least one anionic surfactant preferably selected from linear alkylbenzenesulfonates (LAS), alpha-olefinsulfonates (AOS) and alcohol ethersulfates (AES or AEOS or FES, also known as alcohol ethoxysulfates or fatty alcohol ether sulfates).

A polypeptide having hexosaminidase activity may be obtained from microorganisms of any genus. The hexosaminidases having beta-N-acetylglucosaminidase activity are preferably selected from any of those listed below.

The polypeptides useful in the present invention belonging to the Glycoside Hydrolase family 20 (GH20, www.cazy.org). This family includes dispersins such as Dispersin B (DspB) which is β-N-acetylglucosamininidases belonging to the Glycoside Hydrolase 20 family. One aspect of the invention relates to a composition for cleaning a medical device comprising;
a) at least 0.01 mg/mL hexosaminidases having beta-N-acetylglucosaminidase activity, wherein the hexosaminidases is selected for the group consisting of: a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 2, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 3, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 4, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 5, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 6, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 7, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 8, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 9, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 10, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 11, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 12, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 13, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 14, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 15, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 16, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 17, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 18, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 19, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 20, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 21, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 22, a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 23, and a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids sequence shown in SEQ ID NO: 24;

b) at least one cleaning component, preferably selected from the group consisting of: surfactants, builders, bleach components, polymers and dispersing agents, preferably wherein the composition comprises, at least one anionic surfactant preferably selected from the group consisting of: linear alkylbenzenesulfonates (LAS), alpha-olefinsulfonates (AOS) and alcohol ethersulfates (AES or AEOS or FES, also known as alcohol ethoxysulfates or fatty alcohol ether sulfates).

The hexosaminidase may be included in the cleaning e.g. detergent composition of the present invention at a level of at least 0.0001 to at least 100, at least 0.001 to at least 100, at least 0.01 to at least 100, at least 0.02 to at least 100, at least 0.01 to at least 100, at least 0.1 to at least 100, at least 0.2 to at least 100, at least 0.5 to at least 100 mg/mL, preferably, the concentration of hexosaminidase enzyme in the cleaning composition e.g. detergent is in the range 0.01 to 100, 0.1 to 50 or 1 to 10 mg/mL. The detergent composition may comprise at least 0.00008%, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of hexosaminidase enzyme.

The choice of adjunct ingredients e.g. cleaning components may include consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The composition preferably comprises one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01 to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-01), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The composition may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxid—eurea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of the compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes. In some embodiments, where a source of a peracid is included, an organic bleach catalyst or bleach booster may be used having one of the following formulae:

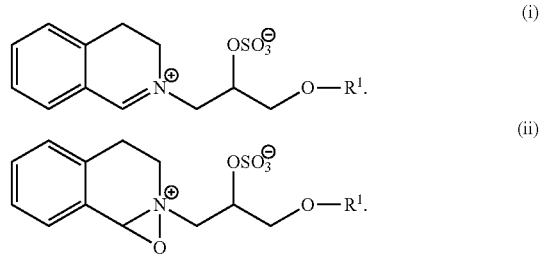

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The composition of the present invention may also include fabric hueing agents such as dyes or pigments, which when formulated in detergent compositions can deposit onto a fabric when the fabric is contacted with a wash liquor comprising the detergent compositions and thus altering the tint of the fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Proteases

Suitable proteases for the compositions of the invention include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867. *Subtilisin lentus, Subtilisin* Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/Genencor Int.) such as those derived from *Bacillus amyloliquefaciens*.

Examples of useful proteases are the variants described in: WO89/06279, WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO: 1 of WO 2016/001449. More preferred the protease variants may comprise one or more of the mutations selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO: 1 of WO 2016/001449, the *Bacillus amylolichenifaciens* protease (BPN') shown in SEQ ID NO: 2 of WO2016/001449. The protease variants preferably have at least 80% sequence identity to SEQ ID NO: 1 or SEQ ID NO: 2 of WO 2016/001449.

A protease variant comprising a substitution at one or more positions corresponding to positions 171, 173, 175, 179, or 180 of SEQ ID NO: 1 of WO2004/067737, wherein the protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™' Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes NS).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes NS).

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from B. amyloliquefaciens shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K
wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus™, Natalase™, Liquozyme X and BAN™ (from Novozymes NS), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases include those comprised by the enzyme classification EC 1.11.1.7, as set out by the Nomenclature Committee of the International Union of Biochemistry and Molecular Biology (IUBMB), or any fragment derived therefrom, exhibiting peroxidase activity. Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257. A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*. Haloperoxidases have also been isolated from bacteria such as *Pseudomonas*, e.g., *P. pyrrocinia* and *Streptomyces*, e.g., *S. aureofaciens*. A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The composition of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The composition of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The composition of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2, 2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The composition of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The composition of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The composition of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Cleaning Products

The composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Definitions

Adjunct ingredients: The term "Adjunct ingredient" means in the present context an additional substance added to a composition and which is normally not an essential part of the composition. In the context of the presence invention an adjunct may also be termed excipient and means the same. In the present context, the terms cleaning ingredient or adjunct and pharmaceutical ingredient or adjunct are used. The person skilled in the art would realize that cleaning adjuncts are adjuncts particularly suitable for cleaning compositions e.g. surfactants, builders etc. and similar for a pharmaceutical ingredient. The term adjunct ingredient includes ingredients suitable for cleaning compositions (also termed cleaning components) and adjunct ingredients suitable for pharmaceutical compositions (also termed excipient). Some ingredients for cleaning and pharmaceutical compositions may be the same.

Anti-biofouling: Biofouling is the accumulation of organic matter such as microorganisms on surfaces. Anti-biofouling is the ability to reduce, remove or prevent biofouling. Thus, an anti-biofouling composition have the ability to reduce, remove or prevent biofouling.

Biofilm: The term "Biofilm" means organic matter produced when any group of microorganisms cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides e.g. PNAG. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On surfaces biofilm producing bacteria can be found among the following species: *Acinetobacter* sp., *Aeromicrobium* sp., *Brevundimonas* sp., *Microbacterium* sp., *Micrococcus* sp., *Pseudomonas* sp., *Staphylococcus* sp., *Enterococcus* sp. *Streptococcus* sp. and *Stenotrophomonas* sp. On hard surfaces biofilm producing bacteria may be found among the following species: *Staphylococcus* e.g. *Staphylococcus aureus* or *Staphylococcus epidermidis*, *Pseudomonas* e.g. *Pseudomonas aeruginosa*, *Enterococcus* e.g. *Enterococcus faecalis*, *Streptococcus* e.g. *Streptococcus pneumoniae*, *Acinetobacter* sp., *Aeromicrobium* sp., *Brevundimonas* sp., *Microbacterium* sp., *Micrococcus luteus* and *Stenotrophomonas* sp.

Cleaning adjunct ingredient: The detergent adjunct ingredient (or cleaning component) is different to the hexosaminidase. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning Composition: The term "cleaning composition" refers to compositions that find use in the removal of undesired compounds from items to be cleaned, such as textiles. The cleaning composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains present on the object to be cleaned during e.g. wash or hard surface cleaning.

By the term "medical device" is meant any medical device suitable for cleaning, reprocessing and reuse, such as, but not limited to an endoscope, encephaloscope, laryngoscope, esophagoscope, thoracoscope, nasopharyngoscope, angioscope, nephroscope, colonoscope, proctoscope, arthroscope, rhinoscope, esophagoscope, bronchoscope, pancreatoscope, mediastinoscope, gastroscope, laparoscope, amnioscope, cystoscope, a hysteroscope, choledochoscope or accessories for any of the scopes listed. The medical device may be selected from the group consisting of a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.

By the term "pharmaceutical adjunct ingredient" means any pharmaceutical excipient suitable for formulating the pharmaceutical compound. Such excipients, carriers, vehicles etc. are well known to those of skill in the art and are described in text books such as Remington's Pharmaceutical Sciences, Mack Publishing Co., Easton, Pa., 1985. Pharmaceutically acceptable excipients which are suitable for use in tablet formulations include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. For hard gelatin capsule formulations, the active ingredient can be mixed with an inert solid diluent, for example, calcium carbonate, calcium phosphate or kaolin. For soft gelatin capsule formulations the active ingredient can be mixed with water or an oil medium, for example peanut oil, liquid paraffin or olive oil. Excipients suitable for the manufacture of aqueous suspensions include suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters obtained from fatty acids and a hexitol such as polyoxyethylene sorbitol monooleate, or condensation products of ethylene oxide with partial esters obtained from fatty acids and hexitol anhydrides, for example polyethylene sorbitan monooleate. Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin. Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavouring agents may be added. These compositions may be preserved by the addition of an antioxidant such as ascorbic acid.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment).

The invention is further described in the nonlimiting paragraphs below.

1. A method of cleaning a medical device, wherein the method comprises
   a) contacting the medical device with the composition comprising a hexosaminidase having beta-N-acetylglucosaminidase activity, for a period effective to clean the medical device;
   b) cleaning, the medical device; and
   c) optionally disinfect the medical device.
2. The method according to paragraph 1, wherein the composition comprising at least one adjunct ingredient.
3. The method according to paragraph 2, wherein the adjunct ingredient is selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.
4. The method according to any of the preceding paragraphs, wherein the composition is an anti-biofouling composition.
5. The method according to paragraph 4, wherein the composition comprises a fungicide or biocide preferably a biocidal quaternary ammonium biocide.
6. The method according to any of the preceding paragraphs, wherein the composition is a cleaning or pharmaceutical composition.
7. The method according to any of the preceding paragraphs, wherein the composition is a cleaning composition and wherein the adjunct ingredient is selected from at least one or more cleaning component optionally selected from surfactants, builders, bleach components, polymers, dispersing agents.
8. The method according to paragraph 7, wherein the composition comprises;
   a) at least 0.01 mg/mL hexosaminidases having beta-N-acetylglucosaminidase activity;
   b) at least one cleaning component, preferably selected from surfactants, builders, bleach components, polymers and dispersing agents.
9. The method according to paragraph 8 wherein the composition comprises at least one anionic surfactant selected from linear alkylbenzenesulfonates (LAS), alpha-olefinsulfonates (AOS) or alcohol ethersulfates (AES or AEOS or FES, alcohol ethoxysulfates or fatty alcohol ether sulfates).
10. The method according to any of the preceding paragraphs wherein the medical device is selected from the group consisting of a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.
11. The method according to any of the preceding paragraphs wherein the hexosaminidase having beta-N-acetylglucosaminidase activity is selected from the group consisting of;
    i) a polypeptide comprising the amino acid sequence shown in SEQ ID NO: 1 or a polypeptide having at least 80% sequence identity hereto,
    ii) a polypeptide comprising the amino acid sequence shown in SEQ ID NO: 2 or a polypeptide having at least 80% sequence identity hereto,
    iii) a polypeptide comprising the amino acid sequence shown in SEQ ID NO: 3 or a polypeptide having at least 80% sequence identity hereto,
    iv) a polypeptide comprising the amino acid sequence shown in SEQ ID NO: 4 or a polypeptide having at least 80% sequence identity hereto,
    v) a polypeptide comprising the amino acid sequence shown in SEQ ID NO: 5 or a polypeptide having at least 80% sequence identity hereto,
    vi) a polypeptide comprising the amino acid sequence shown in SEQ ID NO: 6 or a polypeptide having at least 80% sequence identity hereto,
    vii) a polypeptide comprising the amino acid sequence shown in SEQ ID NO: 7 or a polypeptide having at least 80% sequence identity hereto, viii) a polypeptide comprising the amino acid sequence shown in SEQ ID NO: 8 or a polypeptide having at least 80% sequence identity hereto,
ix) a polypeptide comprising the amino acid sequence shown in SEQ ID NO: 9 or a polypeptide having at least 80% sequence identity hereto,
x) a polypeptide comprising the amino acid sequence shown in SEQ ID NO: 10 or a polypeptide having at least 80% sequence identity hereto,
xi) a polypeptide comprising the amino acid sequence shown in SEQ ID NO: 11 or a polypeptide having at least 80% sequence identity hereto,
xii) a polypeptide comprising the amino acid sequence shown in SEQ ID NO: 12 or a polypeptide having at least 80% sequence identity hereto,
xiii) a polypeptide comprising the amino acid sequence shown in SEQ ID NO: 13 or a polypeptide having at least 80% sequence identity hereto,
xiv) a polypeptide comprising the amino acid sequence shown in SEQ ID NO: 14 or a polypeptide having at least 80% sequence identity hereto,
xv) a polypeptide comprising the amino acid sequence shown in SEQ ID NO: 15 or a polypeptide having at least 80% sequence identity hereto,
xvi) a polypeptide comprising the amino acid sequence shown in SEQ ID NO: 16 or a polypeptide having at least 80% sequence identity hereto,
xvii) a polypeptide comprising the amino acid sequence shown in SEQ ID NO: 17 or a polypeptide having at least 80% sequence identity hereto, and
xviii) a polypeptide comprising the amino acid sequence shown in SEQ ID NO: 18 or a polypeptide having at least 80% sequence identity hereto.

12. The method according to paragraph 11, wherein the hexosaminidase having beta-N-acetylglucosaminidase activity is obtained from *Terribacillus* and is selected from the group consisting of; a polypeptide comprising the amino acid sequence shown in SEQ ID NO: 1 or a polypeptide having at least 80% sequence identity hereto, a polypeptide comprising the amino acid sequence shown in SEQ ID NO: 2 or a polypeptide having at least 80% sequence identity hereto, a polypeptide comprising the amino acid sequence shown in SEQ ID NO: 3 or a polypeptide having at least 80% sequence identity hereto, a polypeptide comprising the amino acid sequence shown in SEQ ID NO: 4 or a polypeptide having at least 80% sequence identity hereto, and a polypeptide comprising the amino acid sequence shown in SEQ ID NO: 5 or a polypeptide having at least 80% sequence identity hereto.

13. The method according to paragraph 11, wherein the hexosaminidase having beta-N-acetylglucosaminidase activity is obtained from *Curtobacterium* and is selected from the group consisting of; a polypeptide comprising the amino acid sequence shown in SEQ ID NO: 6 or a polypeptide having at least 80% sequence identity hereto, a polypeptide comprising the amino acid sequence shown in SEQ ID NO: 7 or a polypeptide having at least 80% sequence identity hereto, a polypeptide comprising the amino acid sequence shown in SEQ ID NO: 8 or a polypeptide having at least 80% sequence identity hereto, a polypeptide comprising the amino acid sequence shown in SEQ ID NO: 9 or a polypeptide having at least 80% sequence identity hereto, and a polypeptide comprising the amino acid sequence shown in SEQ ID NO: 10 or a polypeptide having at least 80% sequence identity hereto.

14. The method according to paragraph 11, wherein the hexosaminidase having beta-N-acetylglucosaminidase activity is obtained from *Aggregatibacter* or *Actinobacillus* and belong to the Dispersin B group of dispersins and is selected from the group consisting of; a polypeptide comprising the amino acid sequence shown in SEQ ID NO: 11 or a polypeptide having at least 80% sequence identity hereto, a polypeptide comprising the amino acid sequence shown in SEQ ID NO: 12 or a polypeptide having at least 80% sequence identity hereto, a polypeptide comprising the amino acid sequence shown in SEQ ID NO: 13 or a polypeptide having at least 80% sequence identity hereto, a polypeptide comprising the amino acid sequence shown in SEQ ID NO: 14 or a polypeptide having at least 80% sequence identity hereto, a polypeptide comprising the amino acid sequence shown in SEQ ID NO: 15 or a polypeptide having at least 80% sequence identity hereto, a polypeptide comprising the amino acid sequence shown in SEQ ID NO: 16 or a polypeptide having at least 80% sequence identity hereto, a polypeptide comprising the amino acid sequence shown in SEQ ID NO: 17 or a polypeptide having at least 80% sequence identity hereto, and a polypeptide comprising the amino acid sequence shown in SEQ ID NO: 18 or a polypeptide having at least 80% sequence identity hereto.

15. The use of a composition comprising a hexosaminidase having beta-N-acetylglucosaminidase activity and at least one adjunct ingredient for cleaning of a medical device.

16. The use according to paragraph 15, wherein the adjunct ingredient is selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

17. The use according to any of paragraphs 15 to 16, wherein the composition is an anti-biofouling composition.

18. The use according to paragraph 17, wherein the composition comprises a fungicide or biocide preferably a biocidal quaternary ammonium biocide.

19. The use according to any of the preceding paragraphs, wherein the composition is a cleaning composition and wherein the adjunct ingredient is selected from at least one or more cleaning components optionally selected from surfactants, builders, bleach components, polymers, dispersing agents.

20. The use according to paragraph 19, wherein the composition comprises;
a) at least 0.01 mg/mL hexosaminidases having beta-N-acetylglucosaminidase activity;
b) at least one cleaning component, preferably selected from surfactants, builders, bleach components, polymers and dispersing agents.

21. The use according to paragraph 20 wherein the composition comprises at least one anionic surfactant selected from linear alkylbenzenesulfonates (LAS), alpha-olefinsulfonates (AOS) or alcohol ethersulfates (AES or AEOS or FES, alcohol ethoxysulfates or fatty alcohol ether sulfates).

22. The use according to any of paragraphs 15 to 21, wherein the medical device is selected from the group consisting of a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.

23. The use according to any of the paragraphs 15 to 22, wherein the hexosaminidase having beta-N-acetylglucosaminidase activity is selected from the group consisting of;
    i) a polypeptide comprising the amino acid sequence shown in SEQ ID NO: 1 or a polypeptide having at least 80% sequence identity hereto,
    ii) a polypeptide comprising the amino acid sequence shown in SEQ ID NO: 2 or a polypeptide having at least 80% sequence identity hereto,
    iii) a polypeptide comprising the amino acid sequence shown in SEQ ID NO: 3 or a polypeptide having at least 80% sequence identity hereto,
    iv) a polypeptide comprising the amino acid sequence shown in SEQ ID NO: 4 or a polypeptide having at least 80% sequence identity hereto,
    v) a polypeptide comprising the amino acid sequence shown in SEQ ID NO: 5 or a polypeptide having at least 80% sequence identity hereto,
    vi) a polypeptide comprising the amino acid sequence shown in SEQ ID NO: 6 or a polypeptide having at least 80% sequence identity hereto,
    vii) a polypeptide comprising the amino acid sequence shown in SEQ ID NO: 7 or a polypeptide having at least 80% sequence identity hereto,
    viii) a polypeptide comprising the amino acid sequence shown in SEQ ID NO: 8 or a polypeptide having at least 80% sequence identity hereto,
    ix) a polypeptide comprising the amino acid sequence shown in SEQ ID NO: 9 or a polypeptide having at least 80% sequence identity hereto,
    x) a polypeptide comprising the amino acid sequence shown in SEQ ID NO: 10 or a polypeptide having at least 80% sequence identity hereto,
    xi) a polypeptide comprising the amino acid sequence shown in SEQ ID NO: 11 or a polypeptide having at least 80% sequence identity hereto,
    xii) a polypeptide comprising the amino acid sequence shown in SEQ ID NO: 12 or a polypeptide having at least 80% sequence identity hereto,
    xiii) a polypeptide comprising the amino acid sequence shown in SEQ ID NO: 13 or a polypeptide having at least 80% sequence identity hereto,
    xiv) a polypeptide comprising the amino acid sequence shown in SEQ ID NO: 14 or a polypeptide having at least 80% sequence identity hereto,
    xv) a polypeptide comprising the amino acid sequence shown in SEQ ID NO: 15 or a polypeptide having at least 80% sequence identity hereto,
    xvi) a polypeptide comprising the amino acid sequence shown in SEQ ID NO: 16 or a polypeptide having at least 80% sequence identity hereto,
    xvii) a polypeptide comprising the amino acid sequence shown in SEQ ID NO: 17 or a polypeptide having at least 80% sequence identity hereto, and
    xviii) a polypeptide comprising the amino acid sequence shown in SEQ ID NO: 18 or a polypeptide having at least 80% sequence identity hereto.

24. The use according to paragraph 23, wherein the hexosaminidase having beta-N-acetylglucosaminidase activity is obtained from *Terribacillus* and is selected from the group consisting of; a polypeptide comprising the amino acid sequence shown in SEQ ID NO: 1 or a polypeptide having at least 80% sequence identity hereto, a polypeptide comprising the amino acid sequence shown in SEQ ID NO: 2 or a polypeptide having at least 80% sequence identity hereto, a polypeptide comprising the amino acid sequence shown in SEQ ID NO: 3 or a polypeptide having at least 80% sequence identity hereto, a polypeptide comprising the amino acid sequence shown in SEQ ID NO: 4 or a polypeptide having at least 80% sequence identity hereto, and a polypeptide comprising the amino acid sequence shown in SEQ ID NO: 5 or a polypeptide having at least 80% sequence identity hereto.

25. The use according to paragraph 23, wherein the hexosaminidase having beta-N-acetylglucosaminidase activity is obtained from *Curtobacterium* and is selected from the group consisting of; a polypeptide comprising the amino acid sequence shown in SEQ ID NO: 6 or a polypeptide having at least 80% sequence identity hereto, a polypeptide comprising the amino acid sequence shown in SEQ ID NO: 7 or a polypeptide having at least 80% sequence identity hereto, a polypeptide comprising the amino acid sequence shown in SEQ ID NO: 8 or a polypeptide having at least 80% sequence identity hereto, a polypeptide comprising the amino acid sequence shown in SEQ ID NO: 9 or a polypeptide having at least 80% sequence identity hereto, and a polypeptide comprising the amino acid sequence shown in SEQ ID NO: 10 or a polypeptide having at least 80% sequence identity hereto.

26. The use according to paragraph 23, wherein the hexosaminidase having beta-N-acetylglucosaminidase activity is obtained from *Aggregatibacter* or *Actinobacillus* and belong to the Dispersin B group of dispersins and is selected from the group consisting of; a polypeptide comprising the amino acid sequence shown in SEQ ID NO: 11 or a polypeptide having at least 80% sequence identity hereto, a polypeptide comprising the amino acid sequence shown in SEQ ID NO: 12 or a polypeptide having at least 80% sequence identity hereto, a polypeptide comprising the amino acid sequence shown in SEQ ID NO: 13 or a polypeptide having at least 80% sequence identity hereto, a polypeptide comprising the amino acid sequence shown in SEQ ID NO: 14 or a polypeptide having at least 80% sequence identity hereto, a polypeptide comprising the amino acid sequence shown in SEQ ID NO: 15 or a polypeptide having at least 80% sequence identity hereto, a polypeptide comprising the amino acid sequence shown in SEQ ID NO: 16 or a polypeptide having at least 80% sequence identity hereto, a polypeptide comprising the amino acid sequence shown in SEQ ID NO: 17 or a polypeptide having at least 80% sequence identity hereto, and a polypeptide comprising the amino acid sequence shown in SEQ ID NO: 18 or a polypeptide having at least 80% sequence identity hereto.

27. A method for inhibiting, preventing or treating bacterial or fungal infections comprising administering to an organism a composition comprising at least one hexosaminidase having beta-N-acetylglucosaminidase activity selected from the group consisting of;
  i) a polypeptide comprising the amino acid sequence shown in SEQ ID NO: 1 or a polypeptide having at least 80% sequence identity hereto,
  ii) a polypeptide comprising the amino acid sequence shown in SEQ ID NO: 2 or a polypeptide having at least 80% sequence identity hereto,
  iii) a polypeptide comprising the amino acid sequence shown in SEQ ID NO: 3 or a polypeptide having at least 80% sequence identity hereto,
  iv) a polypeptide comprising the amino acid sequence shown in SEQ ID NO: 4 or a polypeptide having at least 80% sequence identity hereto,
  v) a polypeptide comprising the amino acid sequence shown in SEQ ID NO: 5 or a polypeptide having at least 80% sequence identity hereto,
  vi) a polypeptide comprising the amino acid sequence shown in SEQ ID NO: 6 or a polypeptide having at least 80% sequence identity hereto,
  vii) a polypeptide comprising the amino acid sequence shown in SEQ ID NO: 7 or a polypeptide having at least 80% sequence identity hereto,
  viii) a polypeptide comprising the amino acid sequence shown in SEQ ID NO: 8 or a polypeptide having at least 80% sequence identity hereto,
  ix) a polypeptide comprising the amino acid sequence shown in SEQ ID NO: 9 or a polypeptide having at least 80% sequence identity hereto,
  x) a polypeptide comprising the amino acid sequence shown in SEQ ID NO: 10 or a polypeptide having at least 80% sequence identity hereto,
  xi) a polypeptide comprising the amino acid sequence shown in SEQ ID NO: 11 or a polypeptide having at least 80% sequence identity hereto,
  xii) a polypeptide comprising the amino acid sequence shown in SEQ ID NO: 12 or a polypeptide having at least 80% sequence identity hereto,
  xiii) a polypeptide comprising the amino acid sequence shown in SEQ ID NO: 13 or a polypeptide having at least 80% sequence identity hereto,
  xiv) a polypeptide comprising the amino acid sequence shown in SEQ ID NO: 14 or a polypeptide having at least 80% sequence identity hereto,
  xv) a polypeptide comprising the amino acid sequence shown in SEQ ID NO: 15 or a polypeptide having at least 80% sequence identity hereto,
  xvi) a polypeptide comprising the amino acid sequence shown in SEQ ID NO: 16 or a polypeptide having at least 80% sequence identity hereto,
  xvii) a polypeptide comprising the amino acid sequence shown in SEQ ID NO: 17 or a polypeptide having at least 80% sequence identity hereto, and
  xviii) a polypeptide comprising the amino acid sequence shown in SEQ ID NO: 18 or a polypeptide having at least 80% sequence identity hereto, such that detachment of bacterial or fungal cells from a biofilm is promoted.
28. The method according to paragraph 27, wherein the bacterial or fungal infection to be treated is from a bacterium or fungus that produces a biofilm comprising Poly-N-acetylglucosamine (PNAG).
29. The method according to paragraph 28, wherein the composition comprising a hexosaminidase having beta-N-acetylglucosaminidase activity and an adjunct ingredient is administered as a coating on a medical device implanted in the organism.
30. The method according to any of paragraphs 27 to 29, wherein a wound dressing applied to the subject is impregnated with a composition comprising hexosaminidase having beta-N-acetylglucosaminidase activity.
31. The method according to any of paragraphs 27 to 30, wherein the composition is a pharmaceutical composition.
32. A kit comprising a hexosaminidase an adjunct ingredient and instructions for use.

EXAMPLES

Assays
Assay I: Testing of Hexosaminidase Activity
The hexosaminidase activity of the polypeptides listed in the table below was determined using 4-nitrophenyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 50 mM 2-(N-morpholino)ethanesulfonic acid pH 6 buffer, 1.5 mg/ml 4-nitrophenyl N-acetyl-β-D-glucosaminide and 20 µg/ml purified enzyme sample in a total reaction volume of 100 µl. Blank samples without polypeptide were run in parallel. The reactions were carried out at 37° C. in a Thermomixer comfort (Eppendorf). After 10 minutes of incubation, 5 µl 1 M NaOH was added to each reaction mixture to stop the enzymatic reaction. The absorbance was read at 405 nm using a POLARstar Omega plate reader (BMG LABTECH) to estimate the formation of 4-nitrophenolate ion released because of enzymatic hydrolysis of the 4-nitrophenyl N-acetyl-β-D-glucosaminide substrate.

Composition of Model Detergent a (Liquid)
  Ingredients: 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w).

Composition of Model Detergent B (Liquid)
  Ingredients: 7.2% LAS, 6.6% AEO Biosoft N25-7 (NI), 4.2% AEOS (SLES), 6% MPG (monopropylene glycol), 3% ethanol, 3% TEA, 2.75% coco soap, 2.75% soya soap, 2% glycerol, 1.2% sodium hydroxide, 2% sodium citrate, 1% sodium formate, 0.2% DTMPA and 0.2% PCA (all percentages are w/w).

Composition of Model Detergent MC
A medical cleaning model detergent (model detergent MC) was prepared containing 5% MPG (propylene glycol), 5% Pluronic PE 4300 (PO/EO block polymer; 70%/30%, approx. 1750 g/mol), 2% Plurafac LF 305 (fatty alcohol alkoxylate; C6-10+EO/PO), 1% MGDA (methyl glycine diacetic acid, 1% TEA (triethanolamine) (all percentages are w/w). The pH was adjusted to 8.7 with phosphoric acid.

Example 1 Biofilm Reduction in Liquid Model Detergent

*Staphylococcus aureus* 15981 (kind gift from Iñigo Lasa (Valle et al., Mol Microbiol. 2003 May; 48 (4):1075-87) was used as a model microorganism in the present example. *S. aureus* was restreaked on Tryptone Soya Agar (TSA) (pH 7.3) (CM0131; Oxoid Ltd, Basingstoke, UK) and incubated at 37° C. overnight. A single colony was inoculated into 15 mL of TSB and the culture was incubated 5 hours at 37° C. under shaking conditions. The culture was subsequently diluted (1:100) in fresh TSB+1% glucose (24563; Roquette Freres) and the bacterial suspension was added to 96-well microtiter plates (100 μL aliquots, Thermo Scientific, Nunclon Delta Surface, cat #167008). The plates were incubated for 24 hours at 37° C. under static conditions. After incubation, the biofilm plates were rinsed (100 μL of 0.9% sodium chloride), and the biofilms were treated with model cleaning solution (100 μL, 3.3 g/L Model detergent A or model detergent B in 15° dH water hardness) containing 0 μg/mL (control) or 20 μg/mL enzyme. The hexosaminidase with SEQ ID NO: 17 was used as benchmark. The plates were then incubated at 37° C. for 1 hour, rinsed with water hardness and stained with 0.095% crystal violet (SIGMA V5265) for 15 min. Following the staining, the wells were rinsed and the dye was dissolved with 95% ethanol and the absorbance measured at 595 nm. The results are displayed in table 1, 2 and 3 and 4, as percentages of remaining biofilm after enzymatic treatment compared the benchmark treatment (Absorbance(enzyme)/Absorbance(benchmark) *100%). As clearly seen, the polypeptides display superior biofilm removal as compared to the benchmark, under the tested conditions.

TABLE 1

Biofilm removal in model A detergent compared with the benchmark treatment

| Enzyme | % remaining biofilm (relative to benchmark treatment) |
| --- | --- |
| SEQ ID NO: 18 | 23.4 |
| SEQ ID NO: 11 | 39.4 |
| SEQ ID NO: 12 | 13.8 |
| SEQ ID NO: 13 | 11.5 |
| SEQ ID NO: 14 | 10.0 |
| SEQ ID NO: 15 | 13.5 |
| SEQ ID NO: 16 | 84.3 |
| SEQ ID NO: 1 | 9.6 |
| SEQ ID NO: 6 | 23.5 |
| SEQ ID NO: 2 | 9.3 |

TABLE 2

Biofilm removal in model A detergent compared with the benchmark treatment

| Enzyme | % remaining biofilm (relative to benchmark treatment) |
| --- | --- |
| SEQ ID NO: 7 | 17.1 |
| SEQ ID NO: 4 | 16.1 |
| SEQ ID NO: 9 | 14.8 |
| SEQ ID NO: 8 | 12.6 |
| SEQ ID NO: 5 | 24.6 |
| SEQ ID NO: 10 | 26.8 |

TABLE 3

Biofilm removal in model detergent B compared with the benchmark treatment

| Enzyme | % remaining biofilm (relative to benchmark treatment) |
| --- | --- |
| SEQ ID NO: 3 | 6.8 |

Example 2 Endoscope Cleaning in Liquid Model Detergent

Endoscope biofilms were established using *S. aureus* (Valle et al., Mol Microbiol. 2003 May; 48 (4):1075-87) as follows: The strain was inoculated into 10 mL of TSB and incubated for 6 hours at 37° C. with shaking (200 rpm). After propagation, the culture was diluted (1:100) in fresh TSB+1% glucose (24563; Roquette Freres) and 2 mL aliquots were added to the wells of 24-well polystyrene flat-bottom microplates (144530; Thermo Fisher Scientific) containing sterile pieces (1 cm) of endoscope tubing (4.7 mm diameter, Fluoroelastomer/Viton®, USP Class VI, Endoscopy Development Company, LLC). Sterile medium was added to control wells. After 24 h at 37° C. (static incubation), the endoscope pieces were rinsed with water (6° dH), and treated with 2 ml of a model cleaning solution (3.3 g/L Model detergent A in 6° dH water) containing no enzyme or 10 μg/mL enzyme for 1 hour at 37° C. under static conditions. The endoscope pieces were then rinsed with 6° dH water and stained with 0.095% crystal violet (SIGMA V5265) for 15 min. Following staining, the endoscope pieces were rinsed twice, blotted on absorbent paper and the remaining dye was dissolved using 95% ethanol. 200 μl aliquots of the suspensions were moved to a 96-well microtiter plate and the absorbance was measured at 595 nm. The results are displayed in table 4 as percentage of remaining biofilm after enzymatic treatment as compared to the control (endoscope biofilm treated without enzyme). The experiment was repeated three times.

TABLE 4

Endoscope cleaning properties in model detergent A

| Enzyme | Enzyme dosage (μg/ml) | Remaining biofilm (% of untreated control) |
| --- | --- | --- |
| No enzyme | 0 | 100.0 |
| SEQ ID NO: 3 | 10 | 21.2 |
| SEQ ID NO: 4 | 10 | 5.7 |

The results show that the polypeptides of the invention have endoscope cleaning properties i.e. disrupt and/or remove the biofilm or components of the biofilm tested when compared to samples comprising no enzyme.

Example 3 Cleaning in Medical Cleaning Model Detergent

*S. aureus* 15981 was used as a model microorganism in the present example. The strain was inoculated into 10 mL of TSB+1% glucose (24563; Roquette Freres) and incubated for 16 hours at 37° C., 200 rpm. After propagation, the culture was diluted (1:100) in fresh TSB+1% glucose and 500 μL aliquots were added to the wells of 48-well polystyrene flat-bottom microplates (150787; Thermo Fisher Scientific). Sterile medium was added to control wells. After 16 h at 37° C. (static incubation), the microplates were rinsed with water hardness (5° dH), and treated with a model medical cleaning solution (0.5 g/L Model detergent MC in 5° dH water hardness) containing no enzyme or 2 μg/mL enzyme for 1 hour at 37° C. under static conditions. The microplates were then rinsed with 5° dH water and stained with 0.095% crystal violet (SIGMA V5265) for 15 min. Following staining, the plates pieces were rinsed twice and the remaining dye was dissolved (using 1 vol:1 vol 95% ethanol:30% Acetic acid). 200 μl aliquots of the suspensions were moved to 96-well microtiter plates and the absorbance was measured at 595 nm. The results are displayed in table 5 as percentages of remaining biofilm after enzymatic treatment as compared to the control (biofilm treated without enzyme). The experiment was repeated three times.

TABLE 5

Cleaning properties in medical cleaning model detergent

| Enzyme | Enzyme dosage (µg/ml) | Remaining biofilm (% of untreated control) |
| --- | --- | --- |
| SEQ ID NO: 3 | 2 | 2.0 |
| SEQ ID NO: 4 | 2 | 3.1 |
| SEQ ID NO: 19 | 2 | 2.5 |

TABLE 5-continued

Cleaning properties in medical cleaning model detergent

| Enzyme | Enzyme dosage (µg/ml) | Remaining biofilm (% of untreated control) |
| --- | --- | --- |
| SEQ ID NO: 21 | 2 | 3.8 |
| SEQ ID NO: 23 | 2 | 2.2 |
| SEQ ID NO: 24 | 2 | 2.0 |
| SEQ ID NO: 22 | 2 | 1.9 |

The results show that the polypeptides of the invention have cleaning properties in a medical cleaning relevant detergent i.e. disrupt and/or remove the biofilm or components of the biofilm tested when compared to samples treated with the cleaning solution comprising no enzyme.

What is claimed is:

1. A method of cleaning a medical device, wherein the method comprises
   a) contacting the medical device with the composition comprising a hexosaminidase having beta-N-acetylglucosaminidase activity, for a period effective to clean the medical device; and
   b) cleaning the medical device.

2. The method according to claim 1, wherein the composition comprises at least one adjunct ingredient.

3. The method according to claim 2, wherein the adjunct ingredient is selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

4. The method according to claim 1, wherein the composition is an anti-biofouling composition.

5. The method according to claim 4, wherein the composition comprises a fungicide or biocide.

6. The method according to claim 1, wherein the composition is a cleaning or pharmaceutical composition.

7. The method according to claim 1, wherein the composition is a cleaning composition and wherein the adjunct ingredient is at least one cleaning component selected from the group consisting of surfactants, builders, bleach components, polymers, and dispersing agents.

8. The method according to claim 7, wherein the composition comprises:
   a) at least 0.01 mg/mL hexosaminidase having beta-N-acetylglucosaminidase activity; and
   b) at least one cleaning component.

9. The method according to claim 8 wherein the composition comprises at least one anionic surfactant selected from the group consisting of linear alkylbenzenesulfonates (LAS), alpha-olefinsulfonates (AOS), and alcohol ethersulfates.

10. The method according to claim 1, wherein the medical device is selected from the group consisting of a central venous catheter, an intravascular catheter, a urinary catheter, a Hickman catheter, a peritoneal dialysis catheter, an endrotracheal catheter, a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.

11. The method according to claim 1, wherein the hexosaminidase having beta-N-acetylglucosaminidase activity is selected from the group consisting of:

i) a polypeptide comprising the amino acid sequence shown in SEQ ID NO: 1 or a polypeptide having at least 80% sequence identity thereto, ii) a polypeptide comprising the amino acid sequence shown in SEQ ID NO: 2 or a polypeptide having at least 80% sequence identity thereto, iii) a polypeptide comprising the amino acid sequence shown in SEQ ID NO: 3 or a polypeptide having at least 80% sequence identity thereto, iv) a polypeptide comprising the amino acid sequence shown in SEQ ID NO: 4 or a polypeptide having at least 80% sequence identity thereto, v) a polypeptide comprising the amino acid sequence shown in SEQ ID NO: 5 or a polypeptide having at least 80% sequence identity thereto, vi) a polypeptide comprising the amino acid sequence shown in SEQ ID NO: 6 or a polypeptide having at least 80% sequence identity thereto, vii) a polypeptide comprising the amino acid sequence shown in SEQ ID NO: 7 or a polypeptide having at least 80% sequence identity thereto, ix) a polypeptide comprising the amino acid sequence shown in SEQ ID NO: 9 or a polypeptide having at least 80% sequence identity thereto, x) a polypeptide comprising the amino acid sequence shown in SEQ ID NO: 10 or a polypeptide having at least 80% sequence identity thereto, xi) a polypeptide comprising the amino acid sequence shown in SEQ ID NO: 11 or a polypeptide having at least 80% sequence identity thereto, xii) a polypeptide comprising the amino acid sequence shown in SEQ ID NO: 12 or a polypeptide having at least 80% sequence identity thereto, xiii) a polypeptide comprising the amino acid sequence shown in SEQ ID NO: 13 or a polypeptide having at least 80% sequence identity thereto, xiv) a polypeptide comprising the amino acid sequence shown in SEQ ID NO: 14 or a polypeptide having at least 80% sequence identity thereto, xv) a polypeptide comprising the amino acid sequence shown in SEQ ID NO: 15 or a polypeptide having at least 80% sequence identity thereto, xvi) a polypeptide comprising the amino acid sequence shown in SEQ ID NO: 16 or a polypeptide having at least 80% sequence identity thereto, xvii) a polypeptide comprising the amino acid sequence shown in SEQ ID NO: 17 or a polypeptide having at least 80% sequence identity thereto, xviii) a polypeptide comprising the amino acid sequence shown in SEQ ID NO: 18 or a polypeptide having at least 80% sequence identity thereto, xix) a polypeptide comprising the amino acid sequence shown in SEQ ID NO: 19 or a polypeptide having at least 80% sequence identity thereto, xx) a polypeptide comprising the amino acid sequence shown in SEQ ID NO: 20 or a polypeptide having at least 80% sequence identity thereto, xxi) a polypeptide comprising the amino acid sequence shown in SEQ ID NO: 21 or a polypeptide having at least 80% sequence identity thereto, xxii) a polypeptide comprising the amino acid sequence shown in SEQ ID NO: 22 or a polypeptide having at least 80% sequence identity thereto, xxiii) a polypeptide comprising the amino acid sequence shown in SEQ ID NO: 23 or a polypeptide having at least 80% sequence identity thereto, and xxiv) a polypeptide comprising the amino acid sequence shown in SEQ ID NO: 24 or a polypeptide having at least 80% sequence identity thereto.

12. The method according to claim 11, wherein the hexosaminidase having beta-N-acetylglucosaminidase activity is selected from the group consisting of:

a) a hexosaminidase obtained from *Terribacillus*, selected from the group consisting of polypeptides comprising the amino acid sequence shown in SEQ ID NO: 1, 2, 3, 4, or 5 and polypeptides having at least 80% sequence identity thereto, b) a hexosaminidase obtained from *Curtobacterium*, selected from the group consisting of polypeptides comprising the amino acid sequence shown in SEQ ID NO: 6, 7, 8, 9, or 10 and polypeptides having at least 80% sequence identity thereto, c) a hexosaminidase obtained from *Aggregatibacter* or *Actinobacillus* and belonging to the Dispersin B group of dispersins selected from the group consisting of polypeptides comprising the amino acid sequence shown in SEQ ID NO: 11, 12, 13, 14, 15, 16, 17, or 18 and polypeptides having at least 80% sequence identity thereto, d) a hexosaminidase obtained from *Lactobacillus* selected from the group consisting of polypeptides comprising the amino acid sequence shown in SEQ ID NO: 19, 20, 21 or polypeptides having at least 80% sequence identity thereto, e) a hexosaminidase obtained from *Streptococcus* which is a polypeptide comprising the amino acid sequence shown in SEQ ID NO: 22 or a polypeptide having at least 80% sequence identity thereto, and f) a hexosaminidase obtained from *Staphylococcus* selected from the group consisting of a polypeptide comprising the amino acid sequence shown in SEQ ID NO: 23 or 24 and polypeptides having at least 80% sequence identity thereto.

13. The method according to claim 1, wherein the method further comprises disinfecting the medical device.

14. The method according to claim 1, wherein the hexosaminidase having beta-N-acetylglucosaminidase activity is selected from the group consisting of polypeptides comprising an amino acid sequence having at least 80% sequence identity to SEQ ID NO: 1, SEQ ID NO: 2, SEQ ID NO: 3, SEQ ID NO: 4, or SEQ ID NO: 5.

15. The method according to claim 1, wherein the hexosaminidase having beta-N-acetylglucosaminidase activity is selected from the group consisting of polypeptides comprising an amino acid sequence having at least 85% sequence identity to SEQ ID NO: 1, SEQ ID NO: 2, SEQ ID NO: 3, SEQ ID NO: 4, or SEQ ID NO: 5.

16. The method according to claim 1, wherein the hexosaminidase having beta-N-acetylglucosaminidase activity is selected from the group consisting of polypeptides comprising an amino acid sequence having at least 90% sequence identity to SEQ ID NO: 1, SEQ ID NO: 2, SEQ ID NO: 3, SEQ ID NO: 4, or SEQ ID NO: 5.

17. The method according to claim 1, wherein the hexosaminidase having beta-N-acetylglucosaminidase activity is selected from the group consisting of polypeptides comprising an amino acid sequence having at least 80% sequence identity to SEQ ID NO: 4.

18. The method according to claim 1, wherein the hexosaminidase having beta-N-acetylglucosaminidase activity is selected from the group consisting of polypeptides comprising an amino acid sequence having at least 85% sequence identity to SEQ ID NO: 4.

19. The method according to claim 1, wherein the hexosaminidase having beta-N-acetylglucosaminidase activity is selected from the group consisting of polypeptides comprising an amino acid sequence having at least 90% sequence identity to SEQ ID NO: 4.

* * * * *

UNITED STATES PATENT AND TRADEMARK OFFICE
CERTIFICATE OF CORRECTION

PATENT NO. : 11,505,767 B2
APPLICATION NO. : 16/759648
DATED : November 22, 2022
INVENTOR(S) : Hansen et al.

It is certified that error appears in the above-identified patent and that said Letters Patent is hereby corrected as shown below:

In the Claims

Please amend Claim 11 by inserting the following at Column 100, Line 31:
--iii) a polypeptide comprising the amino acid sequence shown in SEQ ID NO: 8 or a polypeptide having at least 80% sequence identity hereto,--

Signed and Sealed this
Twenty-first Day of February, 2023

Katherine Kelly Vidal
*Director of the United States Patent and Trademark Office*

SEQUENCE LISTING

```
<160> NUMBER OF SEQ ID NOS: 24

<210> SEQ ID NO 1
<211> LENGTH: 324
<212> TYPE: PRT
<213> ORGANISM: Terribacillus saccharophilus

<400> SEQUENCE: 1

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Ala Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Ser Leu Asp Val Gln Asp Phe Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
```

```
                260                 265                 270
Asn Lys Phe Phe Tyr Ile Ser Asp Tyr Tyr Lys Gln Val Asp Thr Pro
                275                 280                 285

Asn Val Lys Gly Ser Ser Leu Val Phe Trp Gly Glu His Ala Asn Asp
                290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 2
<211> LENGTH: 324
<212> TYPE: PRT
<213> ORGANISM: Terribacillus goriensis

<400> SEQUENCE: 2

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
                20                  25                  30

Gly Asp Tyr Leu Gln Leu His Phe Ser Asp Asn Glu Arg Tyr Ala Ile
            35                  40                  45

Ala Ser Glu Phe Leu Gly Gln Asn Gly Glu Asn Pro Asn Ser Thr Tyr
        50                  55                  60

Leu Thr Lys Lys Glu Leu Leu Ser Leu Ile Ala Tyr Ser Asn Asp Arg
65                  70                  75                  80

Asp Ile Met Val Ile Pro Asp Ile Asp Leu Pro Ala His Ser Arg Gly
                85                  90                  95

Trp Leu Asn Ile Met Lys Glu Lys Asp Ser Gly Leu Tyr Thr Asp Ile
                100                 105                 110

Val Thr Asp Tyr Ser Glu Asp Thr Leu Asp Tyr His Asn Asn Ala Val
            115                 120                 125

Ala Leu Tyr Thr Ala Asn Gln Leu Leu Asp Glu Val Leu Asp Leu Phe
        130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
                165                 170                 175

Asn Gln Ile Ala Glu Thr Ala Lys Ala Ser Asn Tyr Lys Pro Gln Met
                180                 185                 190

Trp Asn Asp Ser Ile Thr Pro Glu Gly Ile Gln Asn Leu Asp Arg Ser
            195                 200                 205

Phe Ser Ile Leu Tyr Trp Lys Gln Ser Thr Leu Ser Asn Gly Ala Gln
        210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
                245                 250                 255

Glu Asp Ile Thr Glu Gln Ile Asp Tyr Met Lys Trp Ala Tyr Ala Tyr
                260                 265                 270

Asn Lys Phe Phe Tyr Ile Ser Asp Tyr Tyr Lys Gln Val Asp Thr Ser
            275                 280                 285

Asn Val Lys Gly Ser Ser Leu Val Phe Trp Gly Glu His Ala Asn Asp
        290                 295                 300

Leu Ser Gln Glu Gly Leu Leu Lys Gln Glu Lys Pro Leu Ile Gln Asn
```

```
            305                 310                 315                 320
Phe Leu Gly Leu

<210> SEQ ID NO 3
<211> LENGTH: 324
<212> TYPE: PRT
<213> ORGANISM: Terribacillus saccharophilus

<400> SEQUENCE: 3

Lys Asp Gln Glu Lys Gly Ile Thr Ile Asp Ile Ser Arg Lys Tyr Tyr
1               5                   10                  15

Ser Ile Gly Thr Leu Lys Ala Ile Val Asp Glu Ile Asn Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Thr Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Val Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Ala
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Asp Glu Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Ser Gly Ala Gln
    210                 215                 220

Gly Leu Asp Val Gln Asn Phe Glu Glu Lys Gly Phe Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
    290                 295                 300

Leu Ser Gln Glu Gly Leu Leu Glu Gln Glu Lys Pro Leu Ile Gln Asn
305                 310                 315                 320

Phe Leu Ser Leu

<210> SEQ ID NO 4
<211> LENGTH: 324
<212> TYPE: PRT
<213> ORGANISM: Terribacillus saccharophilus
```

<400> SEQUENCE: 4

```
Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Glu Asn Tyr Ala Ile
        35                  40                  45

Ala Ser Glu Tyr Leu Gly Gln Ser Ser Glu Asn Thr Asn Asn Thr Tyr
    50                  55                  60

Leu Thr Lys Asn Glu Leu Leu Ser Leu Ile Ala Tyr Ser Asn Asp Lys
65                  70                  75                  80

Asp Ile Leu Val Ile Pro Asp Ile Asp Leu Pro Ala His Ser Lys Gly
                85                  90                  95

Trp Leu Glu Leu Ile Lys Lys Lys Asp Val Lys Leu Tyr Asn Asp Ile
            100                 105                 110

Val Thr Asp Tyr Ser Glu Glu Thr Leu Asp Tyr Tyr Asp Asn Arg Val
        115                 120                 125

Ala Leu Asp Thr Val Asn Gln Leu Leu Asp Glu Val Leu Asp Leu Phe
    130                 135                 140

Tyr Gln Pro Lys Phe Glu Gly Lys Gln Arg Ile Val Leu Gly Gly Asp
145                 150                 155                 160

Glu Val Ser Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
            180                 185                 190

Trp Asn Asp Ser Ile Thr Ser Glu Gly Ile Ala Asn Leu Asp Asp Ser
        195                 200                 205

Phe Ser Ile Leu Tyr Trp Gln Gln Ser Thr Leu Ser Ser Gly Glu Glu
    210                 215                 220

Ser Leu Asn Val Glu Asp Phe Glu Asn Trp Gly Phe Ser Val Tyr Asn
225                 230                 235                 240

Tyr Asn Ala Tyr Ser Leu Tyr Phe Leu Pro Ser Asn Gly Phe Thr Gln
                245                 250                 255

Glu Asp Ile Asn Glu Gln Met Asp Tyr Met Asn Trp Ala Tyr Ala His
            260                 265                 270

Asn Lys Phe Phe Tyr Ile Ser Asp Tyr Tyr His Ala Val Glu Thr Ser
        275                 280                 285

Asn Val Lys Gly Ser Ser Leu Thr Phe Trp Gly Glu His Ala Thr Asp
    290                 295                 300

Leu Ser Gln Lys Lys Leu Leu Lys Gln Glu Leu Pro Leu Ile Arg His
305                 310                 315                 320

Tyr Leu Asn Leu

<210> SEQ ID NO 5
<211> LENGTH: 324
<212> TYPE: PRT
<213> ORGANISM: Terribacillus saccharophilus

<400> SEQUENCE: 5

Lys Asp Gln Glu Lys Gly Ile Ser Ile Asp Ile Ser Arg Lys Tyr Tyr
1               5                   10                  15

Ser Ile Gly Thr Leu Lys Ala Ile Asp Glu Ile Ser Ala Asn Gly
            20                  25                  30
```

Gly Asp Tyr Leu Gln Leu His Phe Ser Asp Asn Glu Ser Tyr Ala Ile
            35                  40                  45

Ala Ser Asp Tyr Leu Gly Gln Ile Ser Asp Thr Pro Asn Asn Thr Tyr
 50                  55                  60

Leu Thr Lys Asn Asp Leu Leu Ser Leu Ile Ala Tyr Ser Asn Asp Arg
 65                  70                  75                  80

Asn Ile Leu Ile Ile Pro Asp Met Asp Leu Pro Ala His Ser Arg Gly
                 85                  90                  95

Trp Leu Glu Leu Met Lys Val Lys Asp Arg Glu Leu Tyr Thr Asp Ile
             100                 105                 110

Val Thr Asp Tyr Ser Asn Glu Thr Leu Asp Tyr His Asn Asn Thr Asp
             115                 120                 125

Ala Leu Asn Thr Ala Asn Gln Leu Leu Asn Glu Ile Leu Glu Leu Phe
 130                 135                 140

Tyr Gln Pro Lys Phe Ala Gly Lys Gln Arg Ile Val Leu Gly Gly Asp
145                 150                 155                 160

Glu Val Pro Gly Ser Glu Ile His Gln Leu Asp Phe Ile Arg Phe Ile
                165                 170                 175

Asn Gln Ile Ala Ser Thr Ala Lys Ala Ser Asn Tyr Ala Pro Gln Met
            180                 185                 190

Trp Asn Asp Ser Ile Thr Ala Glu Gly Ile Gln Asn Leu Asp Lys Ser
            195                 200                 205

Phe Ser Ile Leu Tyr Trp Lys Gln Ser Thr Leu Ser Asn Gly Ala Gln
210                 215                 220

Ser Leu Glu Val Gln Asp Phe Glu Asp Trp Asp Phe Pro Val Tyr Asn
225                 230                 235                 240

Tyr Asn Ala Tyr Ser Leu Tyr Phe Leu Pro Ser Ile Arg Phe Thr Asp
                245                 250                 255

Glu Asp Ile Thr Glu Gln Met Asn Tyr Met Lys Trp Ala Tyr Ala Tyr
            260                 265                 270

Asn Lys Phe Phe Tyr Ile Ser Asp Tyr Tyr Lys Ser Val Asp Ala Ser
            275                 280                 285

Asn Val Lys Gly Ser Ser Leu Thr Phe Trp Gly Glu His Ala Thr Asp
290                 295                 300

Leu Ser Gln Glu Glu Leu Leu Glu Gln Glu Leu Pro Leu Ile Lys Lys
305                 310                 315                 320

Phe Leu Ser Leu

<210> SEQ ID NO 6
<211> LENGTH: 461
<212> TYPE: PRT
<213> ORGANISM: Curtobacterium oceanosedimentum

<400> SEQUENCE: 6

Ala Asp Arg Asn Thr Ser Ala Ala Glu Ala Ala Val Thr Ser Ile Ala
 1               5                  10                  15

Pro Arg Ala Thr Ile Thr Gly Val Ala Ala Ile Ser Ala Ala Thr Ser
             20                  25                  30

Ser Arg Thr Thr Val Arg Thr Thr Leu Thr Leu Glu Asn Arg Ser Gly
            35                  40                  45

Glu Arg Glu Ser Ala Ala Asp Ala Trp Leu Tyr Leu Ala Gly Gly Gly
 50                  55                  60

Ala Arg Tyr Ala Leu Gly His Ala Pro Val Arg Ala Leu Ala Ala Gly
 65                  70                  75                  80

Ala Arg Ala Thr Val Arg Thr Thr Leu Arg Val Pro Ser Arg Ala Pro
            85                  90                  95

Ala Gly Lys Tyr Ala Val Leu Ala Cys Ala Gly Pro Tyr Ser Lys Gln
        100                 105                 110

Ala Cys Arg Thr Ser Gly Thr Thr Val Thr Val Gly Thr Ala Ala Arg
        115                 120                 125

Ala Arg Pro Glu Thr Gly Val Met Leu Asp Val Ala Arg Ala Tyr Tyr
130                 135                 140

Pro Val Ser Leu Ile Glu Gln Tyr Val Asp Leu Leu Ala Glu His Gly
145                 150                 155                 160

Gly Gly Phe Leu His Leu His Leu Thr Asp Asp Gln Asn Val Gly Ile
                165                 170                 175

Glu Ser Ala Val Leu Gly Gln Thr Pro Ala Asn Ala Val Leu Arg Asn
            180                 185                 190

Gly Val Tyr Thr Ser Arg Val Thr Gly Arg Pro Phe Leu Ser Ala Ala
        195                 200                 205

Gln Ala Arg Ala Ile Ser Ala Tyr Ala Ala Lys Arg Gly Ile Ala Ile
    210                 215                 220

Val Pro Glu Val Asp Ser Pro Gly His Met Ala Ala Phe Ala Leu
225                 230                 235                 240

Leu Glu Ala Arg His Gly Ala Thr Trp Val Asp Arg Ile Arg Ser Gly
                245                 250                 255

Glu Ser Glu Leu Asp Thr Ser Val Pro Glu Ser Ala Thr Leu Ala Ala
            260                 265                 270

Glu Leu Leu Arg Glu Val Thr Gln Thr Phe Pro Ser Ser Arg Thr Val
        275                 280                 285

His Ile Gly Gly Asp Glu Trp Gly Ala Asp Val Ser Ala Asp Glu Arg
    290                 295                 300

Val Gly Trp Met Asn Ala Met Ala Ala Ile Gly Asp Arg Glu Val
305                 310                 315                 320

Trp Ala Trp Asn Asp Gly Ile Asp Arg Ala Ser Val Gly Arg Leu Asp
                325                 330                 335

Pro Arg Ile His Val Thr Tyr Trp Ser Phe Asp Gly Asp Thr Glu Asp
            340                 345                 350

Ala Ala Glu Arg Arg Glu Arg Ala Arg Arg Ala Ser Ala Thr Asp
        355                 360                 365

Leu Gln Arg Ala Gly Ile Asp Leu Leu Asn Tyr Asn Ser Tyr Tyr Leu
    370                 375                 380

Tyr Glu Val Pro Thr Asp Leu Asp Pro Ala Asp Ser Glu Tyr Thr Val
385                 390                 395                 400

Ala Asp Leu Arg Glu His Trp Ser Leu Arg Ala Trp Asp Gly Asp Ser
                405                 410                 415

Gly Ala Arg Leu Ala Ala Pro Met Ser Gly Ala Ala Val Ala Ile Trp
            420                 425                 430

Gly Glu Asp Leu Asp Gly Ala Pro Ser Glu Ala Leu Leu Arg Trp Ser
        435                 440                 445

Ala Pro His Val Thr Ala Met Ile Glu Thr Ala Ala Ser
    450                 455                 460

<210> SEQ ID NO 7
<211> LENGTH: 445
<212> TYPE: PRT
<213> ORGANISM: Curtobacterium flaccumfaciens

<400> SEQUENCE: 7

```
Asp Thr Ala Val Ser Ala Val Thr Val Thr Lys Val Thr Ala Ser Thr
1               5                   10                  15

Thr Gly Thr Val Val Arg Thr Thr Leu Lys Val Glu Asn Thr Ala Pro
            20                  25                  30

Val Arg Lys Pro Ala Ser Ser Val Trp Leu Tyr Leu Ser Ala Gly Thr
                35                  40                  45

Glu Lys Tyr Thr Leu Gly Arg Val Ala Val Lys Ala Leu Ala Ala Gly
    50                  55                  60

Ser Ser Thr Ser Val Thr Ala Val Arg Gly Thr Pro Ser Arg Ala Ala
65                  70                  75                  80

Ala Gly Lys Tyr Ser Val Leu Ala Cys Ala Gly Ala Tyr Ser Ala Lys
                85                  90                  95

Gln Cys Arg Thr Ser Thr Ala Thr Val Thr Thr Lys Pro Thr Lys Arg
                100                 105                 110

Ala Arg Pro Glu Thr Gly Val Met Leu Asp Val Ala Arg Ala Tyr Tyr
            115                 120                 125

Pro Val Ala Leu Ile Lys Arg Tyr Ile Asp Leu Leu Ala Asp Asp Gly
            130                 135                 140

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
                180                 185                 190

Gln Ala Arg Thr Ile Ser Ala Tyr Gly Ala Glu Arg Gly Val Ala Ile
                195                 200                 205

Val Pro Glu Ile Asp Thr Pro Gly His Met Ala Ala Ala Phe Ala Leu
            210                 215                 220

Leu Glu Ala Gln His Gly Thr Lys Trp Val Asp Arg Ile Arg Ser Gly
225                 230                 235                 240

Glu Asn Glu Leu Asp Thr Ser Ala Pro Glu Ser Leu Ala Leu Ala Lys
                245                 250                 255

Lys Leu Tyr Ala Glu Val Gln Arg Thr Phe Pro Ser Ser Arg Thr Val
                260                 265                 270

His Ile Gly Gly Asp Glu Trp Gly Asp Asp Val Thr Ala Ala Gln Arg
            275                 280                 285

Val Thr Trp Met Asn Ala Met Ala Ala Leu Asp Asp Arg Glu Val
            290                 295                 300

Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
                325                 330                 335

Ala Ala Glu Arg Arg Glu Arg Arg Ala Arg Arg Ala Ser Ala Val Asp
            340                 345                 350

Leu Gln Gln Ala Gly Ile Asp Gln Leu Asn Tyr Asn Ser Tyr Tyr Leu
            355                 360                 365

Tyr Glu Val Pro Thr Asp Leu Asp Pro Ala Asp Ser Asp Tyr Thr Val
            370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Ala Val Ala Ile Trp
                405                 410                 415
```

```
Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
            435                 440                 445

<210> SEQ ID NO 8
<211> LENGTH: 445
<212> TYPE: PRT
<213> ORGANISM: Curtobacterium luteum

<400> SEQUENCE: 8

Asp Thr Ala Val Ser Ala Val Thr Val Thr Lys Val Thr Ala Ser Thr
1               5                   10                  15

Thr Gly Thr Ala Val Arg Thr Thr Leu Lys Val Glu Asn Thr Ala Pro
            20                  25                  30

Val Arg Lys Pro Ala Ser Ser Val Trp Leu Tyr Leu Ser Ala Gly Thr
        35                  40                  45

Glu Lys Tyr Thr Leu Gly Arg Val Ala Val Lys Ala Leu Ser Ala Gly
    50                  55                  60

Ser Ser Thr Ser Val Thr Ala Val Arg Gly Thr Pro Ser Arg Ala Ala
65                  70                  75                  80

Ala Gly Lys Tyr Trp Val Leu Ala Cys Ala Gly Ala Tyr Ser Ala Lys
                85                  90                  95

Gln Cys Arg Thr Ser Thr Ala Thr Val Thr Thr Lys Pro Thr Lys Arg
            100                 105                 110

Ala Arg Pro Glu Thr Gly Val Met Leu Asp Val Ala Arg Ala Tyr Tyr
        115                 120                 125

Pro Val Ala Leu Ile Lys Arg Tyr Ile Asp Leu Leu Ala Asp Asp Gly
    130                 135                 140

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
            180                 185                 190

Gln Ala Arg Thr Ile Ser Glu Tyr Gly Ala Glu Arg Gly Val Thr Ile
        195                 200                 205

Val Pro Glu Ile Asp Thr Pro Gly His Met Ala Ala Ala Phe Ala Leu
    210                 215                 220

Leu Glu Ala Gln His Gly Thr Lys Trp Val Asp Arg Ile Arg Ser Gly
225                 230                 235                 240

Glu Asn Glu Leu Asp Thr Ser Ala Pro Glu Ser Leu Val Leu Ala Lys
                245                 250                 255

Lys Leu Tyr Ala Glu Val Gln Arg Thr Phe Pro Ser Ser Arg Thr Val
            260                 265                 270

His Ile Gly Gly Asp Glu Trp Gly Asp Asp Val Thr Ala Ala His Arg
        275                 280                 285

Val Ala Trp Met Asn Glu Met Ala Ala Thr Leu Gly Asn Arg Glu Val
    290                 295                 300

Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
                325                 330                 335

Ala Ala Glu Arg Arg Glu Arg Arg Ala Arg Arg Ala Ser Ala Val Asp
            340                 345                 350
```

```
Leu Gln Gln Ala Gly Ile Asp Gln Leu Asn Tyr Asn Ser Tyr Tyr Leu
            355                 360                 365

Tyr Glu Val Pro Thr Asp Leu Asp Pro Ala Asp Ser Asp Tyr Thr Val
    370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Ala Val Ala Ile Trp
                405                 410                 415

Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
            435                 440                 445

<210> SEQ ID NO 9
<211> LENGTH: 458
<212> TYPE: PRT
<213> ORGANISM: Curtobacterium oceanosedimentum

<400> SEQUENCE: 9

Ile Gly Gly Ser Ala Gly Thr Ala Asp Ala Ser Gly Ala Pro Arg Leu
1               5                   10                  15

Val Val Thr Lys Val Thr Ala Ser Ser Thr Thr Thr Ser Thr Arg Thr
            20                  25                  30

Thr Val Arg Thr Thr Leu Thr Val Lys Asn Thr Ser Val Ala Arg Lys
        35                  40                  45

Pro Ala Ala Asp Ala Trp Leu Ser Leu Thr Ala Gly Ser Lys Arg Tyr
    50                  55                  60

Thr Leu Gly His Val Ser Val Gln Ser Leu Ala Ala Gly Ala Ser Ala
65              70                  75                  80

Thr Ile His Ala Thr His Thr Ala Pro Pro Arg Ala Pro Ala Gly Lys
                85                  90                  95

Tyr Ala Val Leu Ala Cys Thr Gly Ala Phe Ser Leu Ser Lys Cys Gly
            100                 105                 110

Thr Ser Ala Thr Thr Val Thr Thr Ala Arg Ala Thr Arg Ala Arg Pro
        115                 120                 125

Asp Thr Gly Val Met Leu Asp Val Ala Arg Ala Tyr Tyr Pro Val Ala
    130                 135                 140

Leu Ile Glu Gln Tyr Ile Ala Leu Leu Ala Asp His Gly Gly Arg Phe
145                 150                 155                 160

Leu His Leu His Leu Thr Asp Asp Gln Asn Val Gly Ile Glu Ser Glu
                165                 170                 175

Val Leu Gly Gln Thr Leu Ala Asn Ala Asp Leu Arg Asp Gly Val Tyr
            180                 185                 190

Thr Ser Arg Ile Thr Gly Arg Pro Phe Leu Ser Ala Ala Gln Ala Arg
        195                 200                 205

Glu Ile Ser Arg Tyr Ala Ala Gln Arg Gly Ile Ala Ile Ile Pro Glu
    210                 215                 220

Ile Asp Thr Pro Gly His Met Ala Ala Ala Phe Ala Leu Leu Glu Ala
225                 230                 235                 240

Gly His Gly Lys Gln Trp Val Asp Arg Ile Arg Ser Gly Glu Ser Glu
                245                 250                 255

Leu Asp Thr Ser Ala Pro Gly Ser Ser Ala Leu Ala Ala Arg Leu Leu
            260                 265                 270

Gln Glu Val Thr Arg Thr Phe Pro Ser Ser Arg Thr Val His Ile Gly
```

```
                275                 280                 285
Gly Asp Glu Trp Gly Asp Asp Val Thr Ala Asp Glu Arg Val Gln Trp
290                 295                 300

Leu Asn Thr Met Ala Ala Ala Val Gly Asn Arg Ala Val Trp Ala Trp
305                 310                 315                 320

Asn Asp Gly Ile Asp Arg Ala Ala Ile Gly Arg Leu Asp Pro Arg Ile
                325                 330                 335

His Val Thr Tyr Trp Ser Phe Asp Gly Asp Thr Glu Asp Ala Thr Glu
                340                 345                 350

Arg Arg Glu Arg Arg Glu Arg Arg Ala Gly Ala Asn Asp Leu Tyr Ala
                355                 360                 365

Ala Gly Ile Asp Leu Leu Asn Tyr Asn Ser Tyr Tyr Leu Tyr Glu Val
                370                 375                 380

Pro Thr Asp Leu Asp Ala Ala Asp Ser Glu Tyr Thr Val Ala Asp Leu
385                 390                 395                 400

Arg Glu Asn Trp Ser Leu Arg Thr Trp Asp Gly Asp Ser Gly Ala Arg
                405                 410                 415

Leu Ala Gly Pro Thr Ser Gly Ala Ala Val Ala Ile Trp Gly Glu Asp
                420                 425                 430

Leu Glu Ala Pro Pro Ser Asp Ala Leu Leu Arg Trp Ser Ala Pro His
                435                 440                 445

Val Leu Ala Met Ile Glu Thr Ala Gly Ser
450                 455

<210> SEQ ID NO 10
<211> LENGTH: 450
<212> TYPE: PRT
<213> ORGANISM: Curtobacterium Leaf154

<400> SEQUENCE: 10

Ala Gly Ser Thr Thr Ser Thr Val Thr Val Thr Gln Val Thr Ala Thr
1               5                   10                  15

Thr Thr Ala Ser Ser Thr Gly Thr Ala Val Arg Thr Thr Leu Lys Ile
                20                  25                  30

Lys Asn Thr Ala Ala Val Arg Lys Pro Ala Ser Ser Ala Trp Leu Tyr
                35                  40                  45

Leu Ser Ala Gly Thr Lys Lys Tyr Thr Leu Gly Arg Val Ala Val Lys
50                  55                  60

Ala Leu Ala Ala Gly Ser Ser Thr Ser Val Thr Ala Val Arg Gly Thr
65                  70                  75                  80

Pro Ser Arg Ala Thr Ala Gly Glu Tyr Ser Val Leu Ala Cys Ala Gly
                85                  90                  95

Ala Tyr Ser Ala Lys Gln Cys Arg Thr Ser Thr Ala Thr Val Thr Thr
                100                 105                 110

Lys Pro Thr Lys Arg Ala Arg Pro Glu Thr Gly Val Met Leu Asp Val
                115                 120                 125

Ala Arg Ala Tyr Tyr Pro Val Ala Leu Ile Lys Arg Tyr Ile Asp Leu
130                 135                 140

Leu Ala Asp Asp Gly Gly Arg Phe Leu His Leu His Leu Thr Asp Asp
145                 150                 155                 160

Gln Asn Val Gly Ile Glu Ser Thr Val Leu Gly Gln Thr Leu Ala Asn
                165                 170                 175

Ala Asp Leu Asp Glu Gly Val Tyr Thr Ser Arg Val Thr Arg Arg Pro
                180                 185                 190
```

Phe Leu Ser Ala Ala Gln Ala Arg Thr Ile Ser Asp Tyr Ala Ala Arg
            195                 200                 205

Arg Gly Val Ala Ile Val Pro Glu Ile Asp Thr Pro Gly His Met Thr
210                 215                 220

Ala Ala Phe Asp Leu Leu Glu Ala Gln His Gly Thr Lys Trp Val Asp
225                 230                 235                 240

Arg Ile Arg Ser Gly Glu Asn Glu Leu Asp Thr Ser Thr Pro Gly Ser
            245                 250                 255

Leu Ala Leu Ala Lys Lys Leu Tyr Ala Glu Val Gln Arg Thr Phe Pro
            260                 265                 270

Ala Ser Arg Thr Val His Ile Gly Gly Asp Glu Trp Gly Asp Asp Val
            275                 280                 285

Ser Ala Ala Glu Arg Val Ala Trp Met Asn Ala Met Ala Ala Ala Leu
            290                 295                 300

Gly Asn Arg Glu Val Trp Ala Trp Asn Asp Gly Ile Asp Arg Val Ala
305                 310                 315                 320

Val Gly Arg Leu Asp Pro Arg Ile His Val Thr Tyr Trp Ser Phe Asp
            325                 330                 335

Gly Asp Thr Glu Asp Ala Ala Glu Arg Glu Arg Ala Arg Arg Arg
            340                 345                 350

Ala Ser Ala Val Asp Leu Gln Gln Ala Gly Ile Asp Met Leu Asn Tyr
            355                 360                 365

Asn Ser Tyr Tyr Leu Tyr Glu Val Pro Thr Asp Leu Asp Pro Ala Asp
            370                 375                 380

Ser Glu Tyr Thr Val Ala Asp Leu Arg Glu Asn Trp Ser Leu Arg Thr
385                 390                 395                 400

Trp Asp Gly Asp Ser Gly Ser Leu Leu Ala Ala Pro Met Ser Gly Ala
            405                 410                 415

Ala Val Ala Ile Trp Gly Glu Asp Leu Glu Asp Pro Pro Ser Asp Ala
            420                 425                 430

Leu Leu Arg Trp Ser Ala Pro His Val Thr Ala Met Ile Glu Thr Ala
            435                 440                 445

Ala Ser
   450

<210> SEQ ID NO 11
<211> LENGTH: 359
<212> TYPE: PRT
<213> ORGANISM: Aggregatibacter actinomycetemcomitans

<400> SEQUENCE: 11

Cys Val Lys Gly Asn Ser Ile His Pro Gln Lys Thr Ser Thr Lys Gln
1               5                   10                  15

Thr Gly Leu Met Leu Asp Ile Ala Arg His Phe Tyr Ser Pro Glu Val
            20                  25                  30

Ile Lys Ser Phe Ile Asp Thr Ile Ser Leu Ser Gly Gly Asn Phe Leu
            35                  40                  45

His Leu His Phe Ser Asp His Glu Asn Tyr Ala Ile Glu Ser His Leu
        50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
            115                 120                 125

Asp Arg Gly Ile Lys Tyr Leu Gln Gly Leu Lys Ser Arg Gln Val Asp
        130                 135                 140

Asp Glu Ile Asp Ile Thr Asn Ala Asp Ser Ile Ala Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Ser Thr Phe Glu
210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Ala Asn Gly Asp Glu
        355

<210> SEQ ID NO 12
<211> LENGTH: 346
<212> TYPE: PRT
<213> ORGANISM: Haemophilus sputorum

<400> SEQUENCE: 12

Gln Asn Ser Thr Lys Gln Ser Gly Leu Met Leu Asp Ile Ser Arg Arg
1               5                   10                  15

Phe Tyr Ser Val Glu Thr Ile Lys Gln Phe Ile Asp Asp Ile Ala Gln
            20                  25                  30

Ala Asn Gly Thr Phe Leu His Leu His Phe Ala Asp His Glu Asn Tyr
        35                  40                  45

Ala Leu Glu Ser Thr Phe Leu Asn Gln Arg Ala Glu Asn Ala Ile Val
    50                  55                  60

Gln Asn Gly Ile Tyr Ile Asn Pro Lys Thr Asn Lys Pro Phe Leu Thr
65                  70                  75                  80

Tyr Glu Gln Ile Asp Gln Ile Ile Arg Tyr Ala Gln Glu Lys Gln Ile
                85                  90                  95

Glu Leu Ile Pro Glu Val Asp Ser Pro Ala His Ile Lys Gly Ile Leu
            100                 105                 110

Thr Leu Leu Arg Leu Glu Lys Gly Glu Asp Tyr Val Asn Gln Ile Ala

```
            115                 120                 125
Leu Asn Gln Asp Glu Leu Asn Leu Asp Ser Pro Glu Ser Leu Thr Met
    130                 135                 140

Met Lys Thr Leu Val Asp Glu Val Cys Tyr Ile Phe Gly Tyr Ser Ala
145                 150                 155                 160

Gln His Phe His Ile Gly Gly Asp Glu Phe Asn Tyr Ala Ser Asn Phe
                165                 170                 175

Ile Arg Tyr Val Asn Ala Leu Asn Gln His Ile Asn Gln Lys Gly Leu
            180                 185                 190

Ile Thr Arg Met Trp Asn Asp Gly Leu Leu Gln Gln Asn Ile Asp Glu
        195                 200                 205

Leu Asp Lys Asn Ile Glu Ile Thr Tyr Trp Ser Phe Asp Gly Asp Ala
    210                 215                 220

Gln Glu Lys Asn Asp Ile Val Glu Arg Arg Ala Thr Arg Ile Ser Leu
225                 230                 235                 240

Pro Thr Leu Leu Asp Lys Gly Phe Lys Ala Leu Asn Tyr Asn Ser Tyr
                245                 250                 255

Tyr Leu Tyr Phe Ile Pro Lys Asp Asn Gly Asn Ile Ala Thr Asp Ala
            260                 265                 270

Lys Phe Ala Leu Asn Asp Leu Lys Gln Asn Trp Gln Leu Leu Arg Trp
        275                 280                 285

Asp Gly Asn Tyr Glu Thr Gln Pro Ile Gln Gln Ala Glu Asn Leu Ile
    290                 295                 300

Gly Ala Ala Phe Ser Ile Trp Gly Glu His Ala Gly Lys Leu Ser Asp
305                 310                 315                 320

Asp Val Ile His Gln Ala Thr Ser Pro Leu Ile Gln Ala Thr Ile Ile
                325                 330                 335

Gln Thr Asn Ala Lys Thr Thr Gly Pro Asn
            340                 345

<210> SEQ ID NO 13
<211> LENGTH: 352
<212> TYPE: PRT
<213> ORGANISM: Actinobacillus suis

<400> SEQUENCE: 13

Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Ser Glu Ala Asn Ala
    50                  55                  60

Ile Val Lys Asp Gly Thr Tyr Tyr Asn Pro Lys Thr Asn Lys Pro Phe
65                  70                  75                  80

Leu Thr Tyr Lys Gln Ile His Asp Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Gly Lys Asp Tyr Val Lys Lys
        115                 120                 125

Leu Lys Ser Lys Met Asn Asp Glu Glu Ile Asp Ile Thr Asn Pro Glu
    130                 135                 140
```

```
Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
            165                 170                 175

Ser Val Glu Thr Asn His Glu Phe Ile Ser Tyr Val Asn Thr Leu Asn
            180                 185                 190

Gln Phe Ile Asn Glu Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Glu Ser Gln Asp Ile Ala Glu
225                 230                 235                 240

Arg Arg Lys Ile Arg Ala Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys Tyr Ala Thr Glu Asp Val Leu
        275                 280                 285

Asn Asn Trp Lys Leu Gly Leu Trp Asp Gly Gln Asn Lys Glu Asn Met
290                 295                 300

Val Glu Asn Thr Lys Asn Ile Ile Gly Ser Ser Leu Ser Ile Trp Gly
305                 310                 315                 320

Glu Arg Ser Gly Ser Leu Ser Ser Glu Val Ile Glu Ser Thr Gln
                325                 330                 335

Asp Leu Leu Lys Ala Val Ile Gln Lys Thr Asn Asp Pro Lys Ser His
            340                 345                 350

<210> SEQ ID NO 14
<211> LENGTH: 352
<212> TYPE: PRT
<213> ORGANISM: Actinobacillus capsulatus DSM 19761

<400> SEQUENCE: 14

Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Leu Glu Ala Asn Ala
    50                  55                  60

Ile Val Lys Asp Gly Thr Tyr Tyr Asn Pro Thr Thr Asn Lys Pro Phe
65                  70                  75                  80

Leu Thr Tyr Lys Gln Ile Asn Asp Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Ser Lys Asp Tyr Val Lys Arg
        115                 120                 125

Leu Lys Ser Lys Met Asn Asp Glu Glu Ile Asp Ile Thr Asn Leu Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175
```

Ser Val Glu Thr Asn His Glu Phe Ile Thr Tyr Val Asn Thr Leu Asn
            180                 185                 190

Gln Phe Ile Asn Asn Lys Gly Lys Ile Thr Arg Ile Trp Asn Asp Gly
            195                 200                 205

Leu Ile Lys Asn Leu Asn Gln Leu Asn Lys Asn Val Glu Ile Thr
            210                 215                 220

Tyr Trp Ser Tyr Asp Gly Asp Ala Gln Glu Ser Gln Asp Ile Ala Glu
225                 230                 235                 240

Arg Arg Lys Ile Arg Val Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys His Ala Thr Glu Asp Val Leu
            275                 280                 285

Lys Asn Trp Lys Leu Gly Leu Trp Asp Gly Gln Asn Lys Glu Asn Ile
            290                 295                 300

Val Glu Asn Thr Lys Asn Ile Ile Gly Ser Ser Leu Ser Ile Trp Gly
305                 310                 315                 320

Glu His Ser Gly Ser Leu Ser Ser Ala Val Ile Glu Glu Ser Thr Gln
                325                 330                 335

Glu Leu Leu Lys Ala Val Ile Gln Lys Thr Asn Asp Pro Lys Ser His
            340                 345                 350

<210> SEQ ID NO 15
<211> LENGTH: 352
<212> TYPE: PRT
<213> ORGANISM: Actinobacillus equuli subsp. equuli

<400> SEQUENCE: 15

Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
            35                  40                  45

Asn Tyr Ala Leu Glu Ser Ser Tyr Leu Asp Gln Ser Glu Glu Asn Ala
            50                  55                  60

Ile Val Lys Asp Gly Thr Tyr Tyr Asn Pro Lys Thr Asn Lys Pro Phe
65                  70                  75                  80

Leu Thr Tyr Lys Gln Ile Asp Asp Ile Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Asn Leu Leu Glu Ile Lys His Gly Glu Ala Tyr Val Lys Asn
            115                 120                 125

Leu Lys Ser Lys Met Asn Asp Glu Glu Ile Asp Ile Thr Asn Pro Glu
            130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Ser Tyr Val Asn Thr Leu Asn
            180                 185                 190

Gln Phe Ile Asn Glu Lys Gly Lys Ile Thr Arg Ile Trp Asn Asp Gly

```
                195                 200                 205
Leu Ile Lys Asn Asn Leu Asn Gln Leu Asn Lys Asn Val Glu Ile Thr
            210                 215                 220
Tyr Trp Ser Tyr Asp Gly Asp Ala Gln Lys Ser Gln Asp Ile Ala Glu
225                 230                 235                 240
Arg Arg Lys Ile Arg Ala Asp Leu Pro Glu Leu Leu Glu Asn Gly Phe
                245                 250                 255
Lys Val Leu Asn Tyr Asn Ser Tyr Tyr Leu Tyr Phe Val Pro Lys Gly
            260                 265                 270
Asn Ala Asn Ile Thr His Asp Ser Lys Tyr Ala Thr Glu Asp Val Leu
        275                 280                 285
Asn Asn Trp Lys Leu Gly Leu Trp Asp Gly Lys Asn Lys Glu Asn Glu
    290                 295                 300
Val Lys Asn Thr Lys Asn Ile Ile Gly Ser Ser Leu Ser Ile Trp Gly
305                 310                 315                 320
Glu Arg Ser Gly Ser Leu Ser Ser Glu Val Ile Glu Glu Ser Thr Gln
                325                 330                 335
Asp Leu Leu Lys Ala Val Ile Gln Lys Thr Asn Asp Pro Lys Ser His
            340                 345                 350
```

<210> SEQ ID NO 16
<211> LENGTH: 359
<212> TYPE: PRT
<213> ORGANISM: Aggregatibacter actinomycetemcomitans

<400> SEQUENCE: 16

```
Cys Val Lys Gly Asn Ser Ile Tyr Pro Gln Lys Ile Ser Thr Lys Gln
1               5                   10                  15
Thr Gly Leu Met Leu Asp Ile Ala Arg His Phe Tyr Ser Pro Glu Val
            20                  25                  30
Ile Lys Ser Phe Ile Asp Thr Ile Ser Leu Ser Gly Gly Asn Phe Leu
        35                  40                  45
His Leu His Phe Ser Asp His Glu Asn Tyr Ala Ile Glu Ser His Leu
    50                  55                  60
Leu Asn Gln Arg Ala Glu Asn Ala Val Gln Gly Lys Asp Gly Ile Tyr
65                  70                  75                  80
Ile Asn Pro Tyr Thr Gly Lys Pro Phe Leu Ser Tyr Arg Gln Leu Asp
                85                  90                  95
Asp Ile Lys Ala Tyr Ala Lys Ala Lys Gly Ile Glu Leu Ile Pro Glu
            100                 105                 110
Leu Asp Ser Pro Asn His Met Thr Ala Ile Phe Lys Leu Val Gln Lys
        115                 120                 125
Asp Arg Gly Val Lys Tyr Leu Gln Gly Leu Lys Ser Arg Gln Val Asp
    130                 135                 140
Asp Glu Ile Asp Ile Thr Asn Ala Asp Ser Ile Ala Phe Met Gln Ser
145                 150                 155                 160
Leu Met Asn Glu Val Ile Asp Ile Phe Gly Asp Thr Ser Gln His Phe
                165                 170                 175
His Ile Gly Gly Asp Glu Phe Gly Tyr Ser Val Glu Ser Asn His Glu
            180                 185                 190
Phe Ile Thr Tyr Ala Asn Lys Leu Ser Tyr Phe Leu Glu Lys Lys Gly
        195                 200                 205
Leu Lys Thr Arg Met Trp Asn Asp Gly Leu Ile Lys Ser Thr Phe Glu
    210                 215                 220
```

```
Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
            245                 250                 255

Leu Pro Glu Leu Leu Ala Lys Gly Phe Thr Val Leu Asn Tyr Asn Ser
        260                 265                 270

Tyr Tyr Leu Tyr Ile Val Pro Lys Ala Ser Pro Thr Phe Ser Gln Asp
    275                 280                 285

Ala Ala Phe Ala Ala Lys Asp Val Ile Lys Asn Trp Asp Leu Gly Val
290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Thr Asn Gly Asp Glu
        355
```

<210> SEQ ID NO 17
<211> LENGTH: 359
<212> TYPE: PRT
<213> ORGANISM: Aggregatibacter actinomycetemcomitans

<400> SEQUENCE: 17

```
Cys Val Lys Gly Asn Ser Ile Tyr Pro Gln Lys Thr Ser Thr Lys Gln
1               5                   10                  15

Thr Gly Leu Met Leu Asp Ile Ala Arg His Phe Tyr Ser Pro Glu Val
            20                  25                  30

Ile Lys Ser Phe Ile Asp Thr Ile Ser Leu Ser Gly Gly Asn Phe Leu
        35                  40                  45

His Leu His Phe Ser Asp His Glu Asn Tyr Ala Ile Glu Ser His Leu
    50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Val Lys Tyr Leu Gln Gly Leu Lys Ser Arg Gln Val Asp
    130                 135                 140

Asp Glu Ile Asp Ile Thr Asn Ala Asp Ser Ile Thr Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Asn Thr Phe Glu
    210                 215                 220

Gln Ile Asn Pro Asn Ile Glu Ile Thr Tyr Trp Ser Tyr Asp Gly Asp
225                 230                 235                 240
```

```
Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Thr Asn Gly Asp Glu
            355

<210> SEQ ID NO 18
<211> LENGTH: 351
<212> TYPE: PRT
<213> ORGANISM: Actinobacillus pleuropneumoniae

<400> SEQUENCE: 18

Met Asp Leu Pro Lys Lys Glu Ser Gly Leu Thr Leu Asp Ile Ala Arg
1               5                   10                  15

Arg Phe Tyr Thr Val Asp Thr Ile Lys Gln Phe Ile Asp Thr Ile His
                20                  25                  30

Gln Ala Gly Gly Thr Phe Leu His Leu His Phe Ser Asp His Glu Asn
            35                  40                  45

Tyr Ala Leu Glu Ser Ser Tyr Leu Glu Gln Arg Glu Glu Asn Ala Thr
        50                  55                  60

Glu Lys Asn Gly Thr Tyr Phe Asn Pro Lys Thr Asn Lys Pro Phe Leu
65                  70                  75                  80

Thr Tyr Lys Gln Leu Asn Glu Ile Ile Tyr Tyr Ala Lys Glu Arg Asn
                85                  90                  95

Ile Glu Ile Val Pro Glu Val Asp Ser Pro Asn His Met Thr Ala Ile
            100                 105                 110

Phe Asp Leu Leu Thr Leu Lys His Gly Lys Glu Tyr Val Lys Gly Leu
        115                 120                 125

Lys Ser Pro Tyr Ile Ala Glu Glu Ile Asp Ile Asn Asn Pro Glu Ala
    130                 135                 140

Val Glu Val Ile Lys Thr Leu Ile Gly Glu Val Ile Tyr Ile Phe Gly
145                 150                 155                 160

His Ser Ser Arg His Phe His Ile Gly Gly Asp Glu Phe Ser Tyr Ala
                165                 170                 175

Val Glu Asn Asn His Glu Phe Ile Arg Tyr Val Asn Thr Leu Asn Asp
            180                 185                 190

Phe Ile Asn Ser Lys Gly Leu Ile Thr Arg Val Trp Asn Asp Gly Leu
        195                 200                 205

Ile Lys Asn Asn Leu Ser Glu Leu Asn Lys Asn Ile Glu Ile Thr Tyr
    210                 215                 220

Trp Ser Tyr Asp Gly Asp Ala Gln Ala Lys Glu Asp Ile Gln Tyr Arg
225                 230                 235                 240

Arg Glu Ile Arg Ala Asp Leu Pro Glu Leu Leu Ala Asn Gly Phe Lys
```

```
              245                 250                 255
Val Leu Asn Tyr Asn Ser Tyr Tyr Leu Tyr Phe Val Pro Lys Ser Gly
            260                 265                 270

Ser Asn Ile His Asn Asp Gly Lys Tyr Ala Ala Glu Asp Val Leu Asn
            275                 280                 285

Asn Trp Thr Leu Gly Lys Trp Asp Gly Lys Asn Ser Ser Asn His Val
            290                 295                 300

Gln Asn Thr Gln Asn Ile Ile Gly Ser Ser Leu Ser Ile Trp Gly Glu
305                 310                 315                 320

Arg Ser Ser Ala Leu Asn Glu Gln Thr Ile Gln Gln Ala Ser Lys Asn
                325                 330                 335

Leu Leu Lys Ala Val Ile Gln Lys Thr Asn Asp Pro Lys Ser His
                340                 345                 350

<210> SEQ ID NO 19
<211> LENGTH: 331
<212> TYPE: PRT
<213> ORGANISM: Lactobacillus paraplantarum

<400> SEQUENCE: 19

Asn Ser Ser Thr Leu Asn Thr Ser Gln Gly Val Met Leu Asp Leu Gly
1               5                   10                  15

Arg His Pro Leu Asp Glu Thr Ala Ile Lys Ala Val Ile Ser Ala Ala
            20                  25                  30

Ala Glu Gln His Met Gln Tyr Val Glu Leu His Leu Ser Asp Asn Glu
        35                  40                  45

His Leu Cys Phe Gln Ser Ala Tyr Leu Gly Asn Ala Ala Ser Ala Thr
    50                  55                  60

Val Leu Ser Ala Thr Thr Leu Glu Gln Leu Val Ala Tyr Ala Asn Gln
65                  70                  75                  80

Leu Asn Ile Glu Leu Val Pro Asp Val Asp Leu Pro Ser His Ala Gly
                85                  90                  95

Ala Ile Leu Arg Gln Leu Gln Gln Thr His Pro Asp Ile Tyr Asn Thr
            100                 105                 110

Val Lys Leu Asp Asp Glu Thr Ile Asp Tyr Thr Lys Pro Ala Ala Ile
        115                 120                 125

Ser Leu Ala Thr Thr Leu Tyr Gly Glu Leu Asp Ala Ser Phe Asn Asn
    130                 135                 140

Gln Ser Gln His Asp Leu Met Leu Gly Ala Asp Glu Val Pro Gly Ser
145                 150                 155                 160

Ala Ser Ala Tyr Ile Glu Leu Thr Thr Phe Ile Asn Gln Val Ser Arg
                165                 170                 175

Phe Gln Asn Gln His Gly Phe Asn Thr Ser Ile Trp Asn Asp Ser Leu
            180                 185                 190

Leu Lys Asn Glu Leu Thr Arg Leu Asp Ser Asn Ile Thr Ile Asn Tyr
        195                 200                 205

Trp Ser Gln Ser Gly Asn Asn Thr Asp Val Ala Ile Ile Ala Asp Arg
    210                 215                 220

Tyr Ala Asn Arg Val Ser Val Pro Asp Ile Leu Ala Ser Gly His Pro
225                 230                 235                 240

Ile Val Asn Cys Asn Ser Tyr Ala Thr Tyr Tyr Gln Ile Lys Asn Ile
                245                 250                 255

Gly Asn Val Asn Asp Asp Asp Tyr Phe Ile Asn Tyr Leu Asn His Thr
            260                 265                 270
```

```
Phe Arg Pro Asn Ile Phe Asn Glu Ile Asp Thr Asn Gly His Asn Gln
            275                 280                 285

Asp Trp Thr Ile Glu Asp Gly Val Thr Thr Asn Gly Ile Leu Val Ser
290                 295                 300

Leu Trp Gly Ala Asp Ser Glu His Val Thr Pro Thr Ala Ile Val Asn
305                 310                 315                 320

Phe Ile Lys Arg Met Thr Ile Pro Arg Ser Phe
                325                 330

<210> SEQ ID NO 20
<211> LENGTH: 353
<212> TYPE: PRT
<213> ORGANISM: Lactobacillus apinorum

<400> SEQUENCE: 20

Thr Leu Ala Asp Thr Ser Asn Asp Thr Lys Arg Ile Gly Leu Ser Leu
1               5                   10                  15

Asp Cys Ser Arg Thr Tyr Tyr Ser Pro Ser Thr Ile Lys Lys Tyr Ile
                20                  25                  30

Asp Leu Leu Lys Lys Asp His Gly Thr Tyr Leu Gln Leu His Leu Asn
            35                  40                  45

Asp Asn Glu Arg Tyr Gly Val Glu Ser Ser Thr Leu Gly Gln Thr Thr
50                  55                  60

Gln Asn Ala Thr Leu Lys Asp Gly Val Tyr Tyr Asn Asn Lys Thr His
65                  70                  75                  80

Leu Ala Phe Leu Ser Lys Asn Gln Leu Leu Asp Val Ile Gln Tyr Gly
                85                  90                  95

Tyr Thr His Gly Ile Glu Val Ile Pro Glu Ile Asp Leu Pro Gly His
                100                 105                 110

Ala Gln Ser Ile Phe Lys Leu Leu Ser Tyr Thr Ser Glu Gly Lys Lys
            115                 120                 125

Leu Val Lys Glu Leu Glu Asn Lys Asp Gly Tyr Asn Glu Met Tyr Tyr
130                 135                 140

Asn Lys Gln Ala Thr Ile Asp Phe Ser Lys Lys Leu Leu Ser Glu Tyr
145                 150                 155                 160

Val Gly Met Leu Pro Ser Gly Tyr His Ile Ile Val Gly Ala Asp Glu
                165                 170                 175

Ile Thr Ile Ser Asp Lys Ser Asp Gln Glu Ala Val Val Lys Tyr Ile
            180                 185                 190

Asn Ala Ile Asp Asp Tyr Val Asn Ala Asn His Leu Lys Leu Glu Met
            195                 200                 205

Trp Asn Asp Ser Phe His Lys Ala Val Leu Ser Lys Tyr His Lys Asp
210                 215                 220

Ile Leu Ile Asn Tyr Trp Ser Leu Thr Gly Glu Val Ser Ser Ser Lys
225                 230                 235                 240

Asp Arg Lys Asp Asn Ile Arg Met Arg Ala Thr Leu Pro Glu Leu Asn
                245                 250                 255

Lys Ala Gly Phe Lys Thr Ile Asn Tyr Asn Ser Tyr Tyr Leu Tyr Met
            260                 265                 270

Ile Thr Asp Pro Thr Ser Phe Thr Asn Glu Ser Lys Lys Ile Trp Thr
            275                 280                 285

Ser Glu Phe Lys Lys Trp Lys Met Asn Met Trp Asn Asp Glu Ser Thr
290                 295                 300

Lys Asp Ile Thr Lys Ser Ala Asn Asn Ile Gly Ala Ala Ile Ser Ile
305                 310                 315                 320
```

```
Trp Gly Glu Tyr Pro Asn Gln Tyr Thr Gly Asp Gln Thr Tyr Asn Lys
            325                 330                 335

Thr Tyr Tyr Tyr Val Asp Thr Phe Leu Lys Ala Gln Asp Lys Phe Thr
            340                 345                 350

Lys

<210> SEQ ID NO 21
<211> LENGTH: 331
<212> TYPE: PRT
<213> ORGANISM: Lactobacillus paraplantarum

<400> SEQUENCE: 21

Asn Ser Ser Thr Leu Asn Thr Ser Gln Gly Val Met Leu Asp Leu Gly
1               5                   10                  15

Arg His Pro Leu Asp Glu Thr Ala Ile Lys Ala Val Ile Ser Ala Ala
            20                  25                  30

Ala Glu Gln His Met Gln Tyr Val Glu Leu His Leu Ser Asp Asn Glu
        35                  40                  45

His Leu Cys Phe Gln Ser Ala Tyr Leu Gly Asn Ala Ala Ser Ala Thr
    50                  55                  60

Val Leu Ser Ala Thr Thr Leu Glu Gln Leu Val Ala Tyr Ala Asn Gln
65                  70                  75                  80

Leu Asn Ile Glu Leu Val Pro Asp Val Asp Leu Pro Ser His Ala Gly
                85                  90                  95

Ala Ile Leu Arg Gln Leu Gln Gln Thr His Pro Asp Ile Tyr Asn Thr
            100                 105                 110

Val Lys Leu Asp Asp Glu Thr Ile Asp Tyr Thr Lys Pro Ala Ala Val
        115                 120                 125

Ser Leu Ala Thr Thr Leu Tyr Gly Glu Leu Asp Ala Ser Phe Asn Asn
    130                 135                 140

Gln Ser Gln His Asp Leu Met Leu Gly Ala Asp Glu Val Ser Gly Ser
145                 150                 155                 160

Ala Ser Ala Tyr Ile Glu Leu Thr Thr Phe Ile Asn Gln Val Ser Arg
                165                 170                 175

Phe Gln Asn Gln Asn Gly Phe Asn Thr Ser Ile Trp Asn Asp Ser Leu
            180                 185                 190

Leu Lys Asn Glu Leu Asn Arg Leu Asp Ser Asn Ile Thr Ile Asn Tyr
        195                 200                 205

Trp Ser Gln Ser Gly Asn Asn Thr Asp Ala Ala Ile Ile Ala Asp Arg
    210                 215                 220

Tyr Ala Asn Arg Ala Ser Val Pro Asp Ile Leu Ala Ser Gly His Pro
225                 230                 235                 240

Ile Val Asn Cys Asn Ser Tyr Ala Thr Tyr Tyr Gln Phe Lys Asn Ile
                245                 250                 255

Gly Asn Val Asn Asp Asp Asn Tyr Phe Ile Asn Tyr Leu Asn His Thr
            260                 265                 270

Phe Arg Pro Asn Ile Phe Asn Glu Ile Asp Thr Asn Gly His Asn Gln
        275                 280                 285

Asp Trp Thr Ile Glu Asp Gly Val Thr Thr Asn Gly Ile Leu Val Ser
    290                 295                 300

Leu Trp Gly Ala Asp Ser Glu His Val Thr Pro Thr Ala Ile Val Asn
305                 310                 315                 320

Phe Ile Lys Arg Met Ala Ile Pro Arg Ser Phe
                325                 330
```

<210> SEQ ID NO 22
<211> LENGTH: 482
<212> TYPE: PRT
<213> ORGANISM: Streptococcus merionis

<400> SEQUENCE: 22

```
Gln Glu Pro Ile Val Lys Leu Ser Gly Gly Val Met Val Asp Val Ala
1               5                   10                  15

Arg Arg Tyr Tyr Ser Leu Asn Ser Leu Lys Ser Ile Ile Asp Thr Val
            20                  25                  30

Ser Glu Asn Lys Gly Asp Phe Val His Leu His Leu Thr Asp Asp Gln
        35                  40                  45

Asn Tyr Gly Leu Glu Ser Gln Phe Leu Asn Gln Thr Ala Ser Asn Ala
    50                  55                  60

Ile Tyr Asn Gln Asp Asp Gln Ser Tyr Thr Asn Pro Asn Thr Asn Arg
65                  70                  75                  80

Lys Phe Leu Ser Tyr Gly Gln Leu Ala Glu Leu Lys Ser Tyr Ala Gly
                85                  90                  95

Ser Lys Gly Ile Arg Leu Ile Pro Glu Ile Asp Thr Pro Ala His Thr
            100                 105                 110

Gly Gly Leu Lys Ala Leu Leu Pro Tyr Ala Glu Pro Ala Val Thr Ser
        115                 120                 125

Gln Phe Lys Trp Val Ser Trp Asp Glu Asp Arg Gln Leu Asp Leu Asp
    130                 135                 140

Ala Ala Thr Thr Gln Glu Ala Val Arg Gln Leu Tyr Met Glu Leu Val
145                 150                 155                 160

Arg Glu Leu Pro Gly Leu Glu Tyr Ile His Ile Gly Gly Asp Glu Ile
                165                 170                 175

Ser Gly Gly Leu Ile Gln Gly Gln Ser Phe Ile Ser His Val Asn Gln
            180                 185                 190

Leu Cys Asp Tyr Leu Ala Gly Gln Gly Ile Lys Thr Gln Ile Trp Asn
        195                 200                 205

Asp Ser Leu Ser Arg Gln Leu Leu Pro Ser Leu Asn Arg Asn Val Glu
    210                 215                 220

Ile Ala Tyr Trp Gly Tyr Leu Pro His Arg Asn Pro Asp Leu Ala Thr
225                 230                 235                 240

Ala Ser Asp Leu Ser Asp Gln Asp Phe Lys Leu Leu Asn Tyr Asn Gly
                245                 250                 255

Tyr Tyr Leu Ala Phe Val Pro Lys Pro Ser Glu Lys Leu Gln Ser Asp
            260                 265                 270

Ala Leu Phe Ala Ala Asn Asp Ile Leu Lys Thr Trp Asn Leu Ser Gln
        275                 280                 285

Phe His Met Asp Thr Gly Asp Ser Ile Asn Ser Leu Lys Asn Val Ile
    290                 295                 300

Gly Ala Ala Phe Ser Ile Trp Ser Glu Glu Ser Ala Gly Leu Thr Asp
305                 310                 315                 320

Glu Glu Ile Phe Ser Ala Met Gly Ser Pro Ile Arg Ala Leu Leu Thr
                325                 330                 335

Val Ile Asn Gln Glu Asn Ile Lys Arg Asn Glu Asn Thr Thr Thr Thr
            340                 345                 350

Thr Thr Glu Ser Met Thr Glu Ala Thr Thr Ile Thr Thr Glu Pro
        355                 360                 365

Thr Thr Gln Ser Thr Thr Glu Ser Thr Thr Thr Thr Thr Glu Ser
```

```
                370                 375                 380
Thr Thr Glu Thr Thr Thr Thr Val Thr Thr Glu Ser Thr Thr Lys Ser
385                 390                 395                 400

Thr Thr Glu Gly Thr Thr Glu Thr Thr Thr Pro Ile Pro Pro Met Pro
                405                 410                 415

Gln Pro Thr Thr Ser Pro Glu Thr Ser Thr Ala Thr His Ala Thr Thr
                420                 425                 430

Thr Asn Pro Ser Thr Ser Lys Asp Gly Asn Lys Leu Ser Lys Ser Lys
                435                 440                 445

Arg Ile Leu Pro Ser Thr Gly Glu Thr Ile Gly Val Leu Ser Val Ala
450                 455                 460

Gly Leu Ala Leu Phe Leu Phe Val Gly Leu Thr Tyr Tyr Arg His Lys
465                 470                 475                 480

Lys Asn

<210> SEQ ID NO 23
<211> LENGTH: 323
<212> TYPE: PRT
<213> ORGANISM: Staphylococcus cohnii

<400> SEQUENCE: 23

Gln Asp Phe Gln Lys Gly Ile Asn Val Asp Ile Ala Arg Lys Asp Tyr
1               5                   10                  15

Ser Leu Lys Ser Leu Lys Lys Ile Val Asp Thr Ile His Glu Asn Asn
                20                  25                  30

Gly Asp Tyr Leu Gln Leu His Phe Ser Asp Asn Glu Asn Tyr Ala Ile
            35                  40                  45

Glu Ser Gln Phe Phe Lys His Glu Asn Ile Ala Ser Gln Asn Tyr Leu
50                  55                  60

Ser Gln Gln Glu Leu Lys Asn Leu Ile His Tyr Ser Asn Lys Leu Asn
65                  70                  75                  80

Ile Met Val Val Pro Glu Phe Asp Leu Pro Ser His Ser Lys Ala Trp
                85                  90                  95

Leu Leu Leu Leu Lys Asn Glu Asn Ser Asn Leu His Glu Asn Ile Val
            100                 105                 110

Ser Asp Tyr Ser Asp Glu Thr Ile Asp Phe Phe Ser Asn Gln Lys Ala
        115                 120                 125

Leu Glu Ile Ser Lys Arg Gln Ile Lys Glu Ile Leu Asn Leu Phe His
130                 135                 140

Gln Pro Asn Phe Gln Lys Glu Gln Arg Ile Val Leu Gly Gly Asp Glu
145                 150                 155                 160

Val Pro Gly Gly Lys Ser Tyr Gln Asn Asp Phe Ile Asn Phe Met Asn
                165                 170                 175

Glu Ile Gly Glu Tyr Ala Tyr Gln Asn Gly Tyr Glu Pro Gln Ile Trp
            180                 185                 190

Asn Asp Ser Ile Thr Lys Asn Gly Leu Lys Leu Leu Lys Asn Tyr Phe
        195                 200                 205

Ser Val Ile Phe Trp Lys Gln Ser Asn Asn Glu Asn Asn Glu Pro Gly
210                 215                 220

Ile Thr Val Glu Asp Phe Leu Asp Tyr Asn Phe Lys Val Tyr Asn Tyr
225                 230                 235                 240

Asn Phe Tyr Ser Leu Tyr Phe Leu Pro Ser Lys Asn Tyr Ser Pro Thr
                245                 250                 255

Asp Ile Glu Glu Gln Thr Ser Tyr Ile Ser Trp Ala Tyr Asn His Asn
```

```
                260                 265                 270
Ser Phe Tyr Tyr Leu Lys Asn Pro Tyr Tyr Glu Val Asp Ser Leu Asn
                275                 280                 285

Ile Gln Gly Ser Ala Leu Ser Phe Trp Gly Glu His Ala Thr Gly Met
            290                 295                 300

Arg Glu Glu Glu Val Leu Asn Gln Glu Leu Pro Leu Ile Arg Thr Tyr
305                 310                 315                 320

Leu Asn Lys

<210> SEQ ID NO 24
<211> LENGTH: 321
<212> TYPE: PRT
<213> ORGANISM: Staphylococcus fleurettii

<400> SEQUENCE: 24

Glu Ser Ile Gln Glu Gly Val Ser Val Asp Ile Ala Arg Lys Glu Tyr
1               5                   10                  15

Ser Leu Glu Ser Leu Lys Gln Ile Val Asp Thr Ile His Glu Asn Asn
                20                  25                  30

Gly Gln Tyr Leu Gln Leu His Phe Ser Asp Asp Glu Asn Tyr Ala Ile
            35                  40                  45

Glu Ser Asp Tyr Phe Ser His Gln Gly Ile Pro Asn Glu Asn Tyr Leu
50                  55                  60

Thr Lys Ala Glu Ile Lys Ser Leu Ile Ala Tyr Ser Asn Glu Leu Asn
65                  70                  75                  80

Val Met Val Val Pro Asp Ile Asp Phe Pro Ser His Ser Lys Ala Leu
                85                  90                  95

Leu Ser Leu Ile Lys Asn Glu Asp Lys Asp Leu Tyr Asn Gln Ile Ile
                100                 105                 110

Ser Asp Tyr Ser Asp Asn Thr Phe Asp Phe Phe Ser Asn Asp Lys Ala
            115                 120                 125

Leu Ala Ile Ser Lys Arg His Ile Gly Glu Ile Thr Thr Leu Phe Asn
130                 135                 140

Gln Pro Lys Tyr Asn Gly Gln Gln Arg Ile Val Leu Gly Gly Asp Glu
145                 150                 155                 160

Val Pro Gly Gly Gly Ala Tyr Gln Ser Asp Phe Ile Ser Tyr Met Asn
                165                 170                 175

Asn Ile Gly Ser Tyr Ala Ala Gly Gln Gly Tyr Glu Pro Gln Met Trp
            180                 185                 190

Asn Asp Met Ile Ser His Glu Gly Ile Lys Ser Leu Asn Asp Thr Phe
        195                 200                 205

Ser Ile Leu Tyr Trp Lys Gln Asn Glu Asn Ser Lys Ser Asp Leu Thr
210                 215                 220

Val Glu Asp Phe Ala Glu Tyr Asp Phe Lys Ile Tyr Asn Tyr Asn Phe
225                 230                 235                 240

Tyr Ser Leu Tyr Phe Leu Pro Ser Asn Gln Phe Thr Asn Ala Asp Ile
                245                 250                 255

Glu Glu Gln Ala Asp Tyr Ile Ser Trp Ala Tyr Ala Tyr Asn Lys Phe
            260                 265                 270

Phe Tyr Thr Asn Glu Pro Tyr Gln Glu Val Asp Ser Asp Asn Val Lys
        275                 280                 285

Gly Ser Ala Leu Ser Phe Trp Gly Glu Asp Ala Leu Asn Met Ser Gln
290                 295                 300
```

```
Thr Glu Leu Ile Asn Gln Glu Ile Pro Leu Ile Lys Ala Tyr Phe Ser
305                 310                 315                 320
Ser
```